United States Patent [19]

Duggan

[11] Patent Number: 5,318,593
[45] Date of Patent: Jun. 7, 1994

[54] MULTI-MODE ADAPTABLE IMPLANTABLE PACEMAKER

[75] Inventor: Stephen R. Duggan, Rosemount, Minn.

[73] Assignee: Medtronic, Inc., Minneapolis, Minn.

[21] Appl. No.: 748,226

[22] Filed: Nov. 18, 1991

Related U.S. Application Data

[60] Division of Ser. No. 436,460, Oct. 12, 1989, Pat. No. 5,092,330, which is a division of Ser. No. 127,308, Mar. 5, 1980, Pat. No. 4,958,632, which is a continuation-in-part of Ser. No. 926,303, Jul. 20, 1978, abandoned.

[51] Int. Cl.⁵ .......................................... A61N 1/362
[52] U.S. Cl. ...................................................... 607/9
[58] Field of Search ..................... 128/419 PG; 607/9

[56] References Cited

U.S. PATENT DOCUMENTS

| | | |
|---|---|---|
| 3,311,111 | 3/1967 | Bowers . |
| 3,433,228 | 5/1969 | Keller, Jr. . |
| 3,518,997 | 7/1970 | Sessions . |
| 3,557,796 | 1/1971 | Keller, Jr. . |
| 3,612,041 | 10/1971 | Ragsdale . |
| 3,631,860 | 1/1972 | Lopin . |
| 3,738,371 | 6/1973 | Raddi et al. . |
| 3,738,877 | 1/1974 | Bowers . |
| 3,833,005 | 9/1974 | Wingrove . |
| 3,901,247 | 6/1974 | Walmsley . |
| 3,924,641 | 12/1975 | Weiss . |
| 4,005,282 | 1/1977 | Jennings . |
| 4,126,139 | 11/1978 | Walters et al. . |
| 4,146,029 | 3/1979 | Ellinwood . |
| 4,232,679 | 11/1980 | Schulman . |
| 4,304,238 | 12/1981 | Fischer . |
| 4,958,632 | 9/1990 | Duggan . |

FOREIGN PATENT DOCUMENTS 2738871  3/1978 Fed. Rep. of Germany ...... 128/419

OTHER PUBLICATIONS

RCA Publication "COSMAC Microtutor Summary", pp. 1–11, 26, Sep. 1974.
RCA Publication "Instruction Summary for the CAP 1802 COSMAC Microprocessor", May 1976.

*Primary Examiner*—William E. Kamm
*Attorney, Agent, or Firm*—Reed A. Duthler; Harold R. Patton

[57] ABSTRACT

A multi-mode, adaptable, implantable pacemaker is described including a microprocessor and memory programmed or capable of being programmed with a variety of processes for stimulating the patient's heart and/or for sensing and transmitting to a device external of the patient's body, various conditions of or activities of the patient's heart, or conditions of the pacemaker itself. The pacemaker includes a multiplexer by which a variety of analog and digital inputs are accessed under the control of the microprocessor and operated upon by the processes stored in the memory and executed by the microprocessor. The output of the pacemaker comprises a plurality of latch drivers and switches, which are selectively operable to apply stimulation to the patient's heart, as well as to sense signals indicative of the patient's heart activity as well as other internal conditions. The pacemaker is capable of transmitting these signals via a link such as an RF or acoustical link to an external monitoring apparatus. The external apparatus may transmit code signals to be received by the pacemaker, whereby the pacemaker's memory may be reprogrammed, dependent upon change of the patient's condition. Illustratively, the memory is divided into a plurality of blocks and control signals may be sent from the external apparatus to address the initial or starting location within another block, whereby another, selected program or process may be executed by the microprocessor.

13 Claims, 13 Drawing Sheets

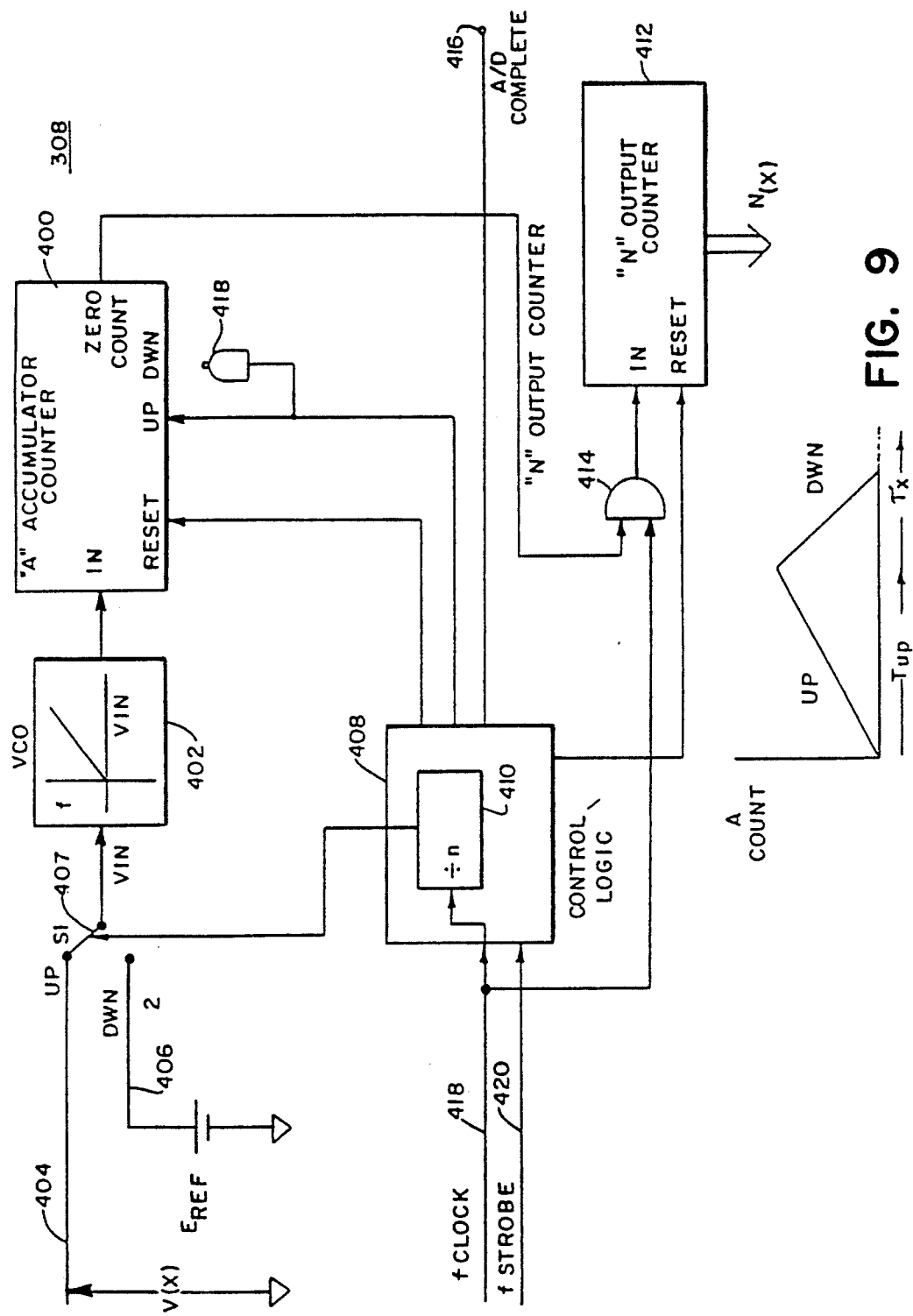

MULTI-MODE ADAPTABLE IMPLANTABLE PACEMAKER

This application is a division of Ser. No. 07/436,460, filed on Oct. 12, 1989, issued as U.S. Pat. No. 5,092,330, which was a divisional application of Ser. No. 06/127,308, filed on Mar. 5, 1980, issued as U.S. Pat. No. 4,958,632, which was a continuation in part of Ser. No. 926,303, filed Jul. 20, 1978, abandoned.

BACKGROUND OF THE INVENTION

1. Field of the Invention

This invention relates to internally implanted electronic devices adapted to be operated in a variety of modes for stimulating body tissue or to monitor various conditions of the device itself or of body tissue, e.g., the patient's heart.

2. Description of the Prior Art

Heart pacers such as that described in U.S. Pat. No. 3,057,356 issued in the name of Wilson Greatbatch and assigned to the assigned of this invention, are known for providing electrical stimulus to the heart whereby it is contracted at a desired rate in the order of 72 beats per minute. Such a heart pacemaker is capable of being implanted within the human body and operative in such an environment for long periods of time. Typically, such pacemakers are implanted in the pectorial region or in the abdominal region of the patient by a surgical procedure, whereby an incision is made in such region and the pacemaker with its own internal power supply, is inserted within the patient's body. This pacer operates asynchronously to provide fixed-rate stimulation not automatically changed in accordance with the body's needs, and has proven effective in alleviating the symptoms of complete heart block. An asynchronous pacer, however, has the possible disadvantage of competing with the natural, physiological pacemaker during episodes of normal sinus condition.

An artificial pacer of the demand type has been developed wherein the artificial stimuli are initiated only when required and subsequently can be eliminated when the heart returns to the sinus rhythm. Such a demand pacer is shown in U.S. Pat. No. 3,478,746 issued Nov. 18, 1969 and entitled "CARDIAC IMPLANTABLE DEMAND PACEMAKER". The demand pacer solves the problem arising in asynchronous pacers by inhibiting itself in the presence of ventricular activity (the ventricle's R wave), but by coming "on line" and filling in missed heartbeats in the absence of ventricular activity.

A problem with such prior art, implantable demand pacers is that there was no way to temporarily increase or decrease the rate or other operating parameter at which these stimulating pulses are generated without surgical intervention. Still another problem is the great difficulty in establishing the battery life remaining, in detecting and correcting a failing electrode, and in establishing an adequate R-wave sensitivity safety margin in an implanted demand pacer.

Some implantable cardiac pacers presently constructed have a rate overdrive capability but do not adequately check the viability of the demand function. Other devices are provided with a magnetic reed switch arrangement which can deactivate the demand amplifier for the purpose of checking the demand function but are lacking in a rate overdrive capability.

Another improvement which has occurred since Greatbatch first disclosed the implantable cardiac pacemaker is means to allow the pacemaker to be reprogrammed after it has been implanted. In U.S. Pat. No. 3,805,796 in the name of Reese Terry, Jr. et al, entitled "Implantable Cardiac Pacer having Adjustable Operating Parameters", which issued in 1974, circuitry is disclosed to allow the rate of the pacemaker to be noninvasively changed after it has been implanted. The rate varies in response to the number of times a magnetically operable reed switch is closed. The Terry et al device operates by counting the number of times the reed switch is closed and storing that count in a binary counter. Each stage of the counter is connected to either engage or bypass one resistor in a serially connected resistor chain, which chain is a part of the RC time constant controlling the pacemaker rate.

The concept of the Terry et al device has been improved upon by the apparatus shown in U.S. Pat. No. 4,066,086 in the name of John M. Adams et al, entitled "Programmable Body Stimulator", which issued in 1978, and which discloses a programmable cardiac pacemaker that responds to the application of radio frequency (RF) pulse bursts while a magnetic field held in close proximity to a magnetically operated reed switch included within the pacemaker package holds the reed switch closed. In the Adams et al circuit, again only the rate is programmable in response to the number of RF pulse bursts applied. The use of radio frequency signals to program cardiac pacemakers was earlier disclosed by Wingrove in the U.S. Pat. No. 3,833,005 entitled "Compared Count Digitally Controlled Pacemaker" which issued in 1974. The Wingrove device was capable of having both the rate and pulse width programmed. However, no pacemaker has ever been described which is capable of having more than two parameters programmed or selected features or tests programmed on command. Such a pacemaker could be called a universally programmable pacemaker.

One area where cardiac pacing technology has lagged behind conventional state of electronic technology involves utilization of digital electrical circuits. One reason for this has been the high energy required to operate digital circuits. However, with more recent technology advances in complimentary metal oxide semiconductor (CMOS) devices fabricated on large scale integrated circuits, together with the improvements of cardiac pacemaker batteries, digital electronic circuits are beginning to be utilized in commercial pacemakers. The inherent advantages of digital circuits are their accuracy, and reliability. Typically, the digital circuit is operated in response to a crystal oscillator which provides a very stable frequency over extended periods of time. There have been suggestions in the prior art for utilizing digital techniques in cardiac stimulators and pacemakers since at least 1966. For instance, see the article by Leo F. Walsh and Emil Moore, entitled "Digital Timing Unit for Programming Biological Stimulators" in *The American Journal of Medical Electronics*, First Quarter, 1977, Pages 29 through 34. The first patent suggesting digital techniques is U.S. Pat. No. 3,557,796 in the name of John W. Keller, Jr., et al, and is entitled "Digital Counter Driven Pacer", which issued in 1971. This patent discloses an oscillator driving a binary counter. When the counter reaches a certain count, a signal is provided which causes a cardiac stimulator pulse to be provided. At the same time the counter is reset and again begins counting the oscillator pulses.

Additionally, in the Keller et al patent, there is disclosed the digital demand concept, in which the counter is reset upon the sensing of a natural heartbeat, and the digital refractory concept, in which the output is inhibited for any certain time after the provision of a cardiac stimulating pulse or the sensing of a natural beat.

As mentioned above, digital programming techniques are shown in both the Terry et al, U.S. Pat. No. 3,805,796 and the Wingrove U.S. Pat. No. 3,833,005. Wingrove additionally discloses digital control circuitry for controlling the rate of the stimulating pulses by providing a resettable counter to continually count up to a certain value that is compared against a value programmed into a storage register. The Wingrove patent also shows provisions for adjusting the output pulse width by switching the resistance in the RC circuit which controls the pulse width.

Other patents disclosing digital techniques useful in cardiac pacing include U.S. Pat. Nos. 3,631,860 in the name of Michael Lopin entitled "Variable Rate Pacemaker, Counter-Controlled, Variable Rate Pacer"; 3,857,399 in the name of Fred Zacouto entitled "Heart Pacer"; 3,865,119 in the name of Bengt Svensson and Gunnar Wallin entitled "Heartbeat Accentuated with Controlled Pulse Amplitude"; 3,870,050 in the name of Wilson Greatbatch entitled "Demand Pacer"; 4,038,991 in the name of Robert A. Walters entitled "Cardiac Pacer with Rate Limiting Means"; 4,043,347 in the name of Alexis M. Renirie entitled "Multiple-Function Demand Pacer with Low Current Drain"; 4,049,003 in the name of Robert A. Walters et al entitled "Digital Cardiac Pacer"; and 4,049,004 in the name of Robert A. Walters entitled "Implantable Digital Cardiac Pacer Having Externally Selectable Operating Parameters and One Shot Digital Pulse Generator for Use Therein".

Though there has been suggested that various parameters, i.e., pulse width and rate, may be changed within an internally implanted pacer, it is desired to provide a device that is capable of operating in various, different pacing and/or sensing modes. The systems of the prior art are capable of storing by means of digital counter circuitry a programmable word indicative of desired rate or pulse width. In an internally implanted device, the space to incorporate a plurality of such counters whereby a number of such functions could be programmed, is indeed limited. Further, there are considerations of the available energy to energize such counters, as well as of the life of its internal power source as a result of the imposed drain. It is well recognized in the art that the complexity of the circuit incorporated within an internally implanted device is limited by many factors including the drain imposed upon the battery and therefore the expected life of a battery before a surgical procedure is required to replace the device's power source, e.g., a battery.

SUMMARY OF THE INVENTION

It is therefore an object of this invention to increase the flexibility and adaptability of an internally implanted device, whereby a plurality of processes including tissue stimulation and telemetry may be effected.

It is a more specific object of this invention to provide an adaptable, multi-purpose implantable pacemaker capable of being programmed before or after implantation to effect a different process of stimulation (or telemetry) dependent upon the patient's present condition.

It is a further object of this invention to provide an internally implanted electrical device having a communication link to transmit signals from and to a transmitter external of the patient's body, whereby control signals may be transmitted to change the process effected by the internal device and data concerning tissue (heart) activity, as well as functions of the implanted device, may be received from the internal device.

In accordance with these and other objects of the invention, there is disclosed an implantable electrical device, such as a heart pacemaker, comprising control means in the form of a digital computer, e.g., a microprocessor, and a memory stored with a plurality of different processes or programs for generating stimulating pulses, executed by the microprocessor, whereby such stimulating pulses are applied to body tissue. Data forming a part of the program stored within the memory determine, for example, the pulse width of and period between the stimulating pulses.

In one aspect of this invention, the heart pacer or pacemaker comprises terminal means for coupling the stimulating pulses to the patient's heart, a clock for providing a series of clock signals, a memory for storing control parameters in the form of a plurality of counts, and a digital control operable in a selected one of a plurality of states and including a counter responsive to the clock signals for counting a selected one of the plurality of count signals and means responsive to the state in which the digital control means is operative for selecting one of the plurality of counts and for successively transferring selected counts from the memory to the counter to be counted whereby the duration of the first and second states of operation of the pacemaker are controlled.

The heart pacer as described above, may be implemented either in permanently coupled (hardwired) digital circuitry or by a microprocessor. For example, in the hardwired embodiment of this invention, the memory comprises a diode matrix having a plurality of input lines, a plurality of output lines, and diodes interconnecting the output and input lines in accordance with the desired counts. In the hardwired embodiment, the digital control means may comprise a mode counter that is advanced after the counter has counted to a predetermined level whereby the next count is selected from the matrix diode and entered into the counter means. In the microprocessor controlled pacemaker, the counter means may be implemented by an addressable location within the memory and there is further included means for addressing selected locations for storing the corresponding first and second counts whereby they are successively loaded into the counter.

In a further aspect of this invention, there is included a pacemaker with an energy source in the form of a battery for energizing the elements of the cardiac pacemaker and means responsive to the voltage level of the energy source for determining which count of a plurality of counts is to be transferred to the counter means. In the above-described microprocessor implemented embodiment, the memory includes a location for receiving and storing a table comprised of a plurality of sets of first and second counts, each set corresponding to a discrete level of the output of the energy source and comparing means for obtaining a match between the output level of the energy source and a corresponding one of the discrete levels for transferring the corresponding set of first and second counts to said counter means to count corresponding periods dependent upon the level of energization of the energy source. In both the microprocessor and hardwired digital embodiments, first and second counts illustratively determining the sense and pulse width periods of a demand mode of pacing are sequentially transferred to a single counter and the count is made dependent upon the level of energization of the energy source, e.g., the pacer's battery.

In a further feature of this invention, there is provided a link between the internally implanted electrical device and an external transmitter, whereby encoded control signals may be transmitted to the internally implanted electrical device, whereby the process effected by the control means is changed or reprogrammed. More specifically, the transmitted control signals may change the address accessed by the microprocessor within the memory, whereby a new process starting at the new address is then executed. Further, it is contemplated that the signals transmitted from the external transmitter may reprogram the memory with a new set of parameters, whereby such variables as pulse width or amplitude, duration between the stimulating pulses, and sense amplifier sensitivity may be changed. In addition, control signals may be transmitted to change the mode of heart pacing, the stored, selectable modes including ventricular demand pacing, asynchronous ventricular pacing, bifocal pacing, atrial synchronous ventricular inhibited pacing (ASVIP), pulse width stretching as a function of power source or battery voltage, automatic threshold following pacing wherein the pulse width of the pacing pulse is adjusted to a minimum width that will achieve heart capture, and multiheart site pacing to disrupt arrhythmias. In addition, the memory may store a program or programs for implementing a plurality of telemetry functions including sensing various heart activities, other body functions and data concerning the operations of the pacer, including providing indications of the actual pulse width, pulse amplitude, interpulse interval, power source current and voltage, moisture content within the implanted device, pacing lead impedance and pacemaker self-test routines.

In a further feature of this invention, the pacemaker includes a multiplexer controlled by the microprocessor for selecting one of a plurality of inputs, whereby signals indicative of the patient's heart activity, e.g., the atrial and ventricular heart activity, other body conditions or conditions such as moisture within the pacemaker, may be selectively applied one at a time to be processed by the microprocessor. A selected output of the multiplexer is applied to an A/D converter and scaling amplifier, whereby the input analog signal is converted to a digital signal and scaled to be processed by the processor.

In a still further feature of this invention, the memory includes a plurality of blocks for respectively receiving a program to be executed by the microprocessor. In such an embodiment, the multiplexer includes inputs for receiving a digitally encoded signal for effecting a change of address, whereby a starting location in a different block may be addressed to effect the execution of the program within that block. It is contemplated that the digitally encoded address signal could be transmitted to the multiplexer of the internally implanted pacemaker via a link from an external transmitter, whereby the physician could change the program being executed by the microprocessor to effect a different mode of patient pacing, dependent upon the present condition of the patient.

In a further feature of this invention, the microprocessor provides output control or timing signals to an array of select switches, each coupled to its own driver and lead. A lead may be coupled from the pacemaker to a particular portion or heart, e.g., the patient's ventricle or atrium, to some other body tissue, to a mechanical transducer to sense body activity or to a transducer within the pacemaker to sense some condition of the pacemaker, e.g., moisture. By selectively closing one of the select switches, that lead is connected, for example, to stimulate body tissue or to receive a signal indicative of a condition to be monitored. Failure of a lead may be overcome by using redundant leads; upon sensing the failure of one lead, a second lead may be connected from the pacemaker to the patient's heart to continue tissue stimulation or monitoring. In one illustrative embodiment of this embodiment, there is included a decoder for sensing and decoding digital signals derived from the pacemaker's memory, to generate and apply control signals to close switches, whereby a selected one of the plurality of switches and leads is coupled to the pacer.

In a still further feature of this invention, there is provided an auto-reset oscillator circuit that is designed to reset the addressing mechanism or register of the microprocessor, whereby if an extraneous noise signal is effective to cause the address register to address a vacant or erroneous location within the system's memory, the process will not be "hung up", but rather will be reset after a predetermined interval to start the process over again. If the addressing mechanism is functioning normally, the microprocessor provides an inhibit signal periodically to the auto-reset oscillator circuit preventing it from applying a reset to the addressing means.

It is a further object of this invention to provide an analog to digital converting apparatus particularly designed to be incorporated within the pacer discussed above. The A/D convertor is implemented in CMOS Technology, in order to impose a minimum drain upon the pacer's power source. While the A/D converter circuitry is controlled by means of clock pulses, it is so configured that the output signal from the A/D converter reflects the analog input signal to the A/D converter, independent of the frequency of the clock signal.

BRIEF DESCRIPTION OF THE DRAWINGS

These and other objects and advantages of the present invention will become more apparent by referring to the following detailed description and accompanying drawings, in which:

FIG. 8 is a functional block diagram of the A/D converter to be incorporated within the pacemaker of FIGS. 6 and 7;

FIG. 9 is a graph illustrating the operation of the up/down counter as shown in FIG. 8;

DETAILED DESCRIPTION OF THE PREFERRED EMBODIMENTS OF THIS INVENTION

Figure 1:
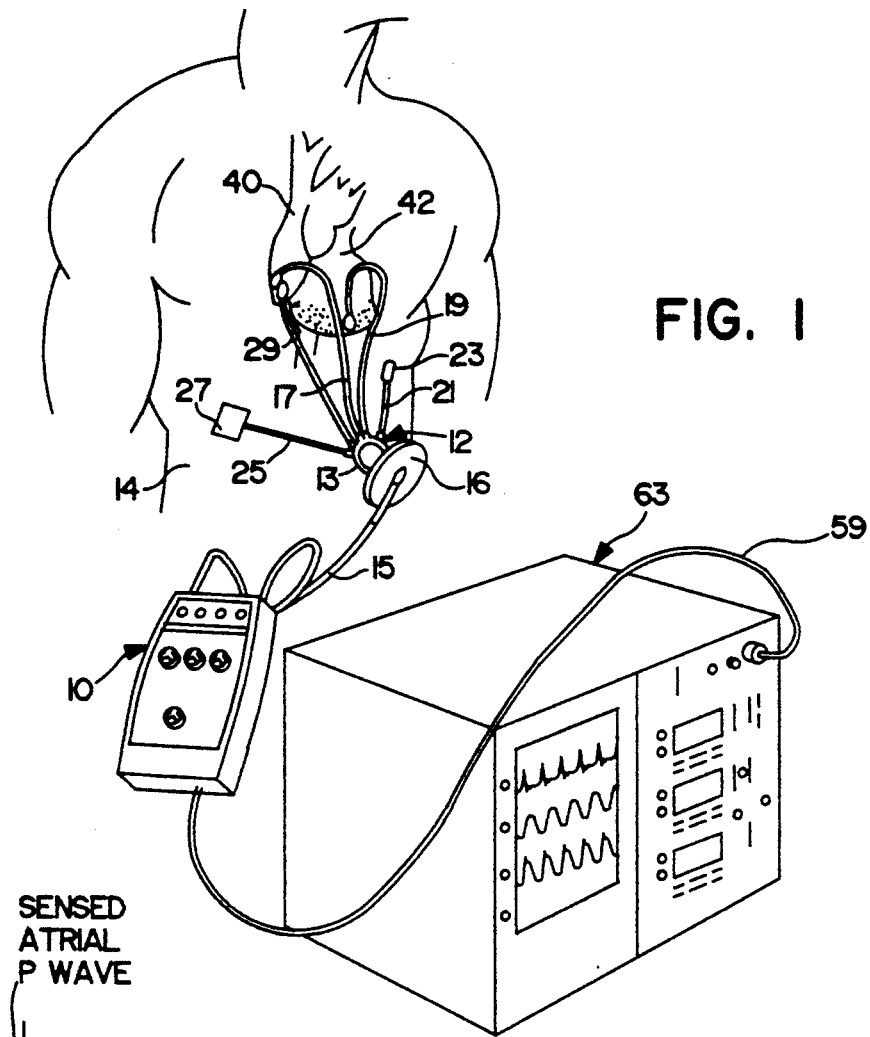
FIG. 1 is a pictorial view of the manner in which the programmable pacemaker of the subject invention is implanted within a patient and in which signals are transmitted thereto and from to respectively change or adapt the program implemented by the implanted pacemaker, as well as to display signals indicative of heart (or other tissue) activity upon an external monitor.

Referring now to the drawings and in particular to FIG. 1, there is shown a pacemaker in accordance with the teachings of this invention adapted to be programmed in a variety of modes in order that the patient's heart including its atrium 40 and its ventricle 42 may be paced in a variety of modes and further, to sense the electrical activity of the patient's atrium and ventricle (or other body tissue) for either modifying pacemaker pacing parameters or for transmission remotely of the patient's body 14.

In particular, the pacemaker 12 includes a body tissue and fluid resistant casing 13, a first lead 17 coupled to and attached by an electrode to the heart's atrium 40, and a second lead 19 coupled to and attached by an electrode to the patient's ventricle 42. Further, there is shown an external transmitter 10 coupled by a lead 15 to a coil or antenna 16 disposed externally of the patient's body 14, for transmitting RF coupled signals to the internally implanted pacemaker 12. Further, there is shown a monitor 63 coupled to the transmitter 10 by a lead 59. As will be explained in detail, the transmitter 10 may be actuated to send signals via the lead 15 and the coil 16, to the internally implanted pacemaker 12, whereby its mode of operation may be changed from one mode to another selected mode; thus, the physician can control the type of pacing imposed upon the patient's heart in accordance with the patient's altered condition. It is understood that at the time of the surgical implantation of the pacemaker 12 within the patient's body 14, that a particular mode of pacing may be desired. Subsequent to the implantation, the patient's condition may change at which time another mode of operation may become desired. Further, it is desired to transmit from the patient's body a variety of signals indicative of various conditions to be sensed and transmitted by the coil 16 and the transmitter 10 to be displayed upon the monitor 63. In addition, as shown in FIG. 1, the internally implanted pacemaker 12 may include a further output and lead 25 coupled to a transducer 27; the transducer 27 may be of a mechanical type for sensing motion of a body organ. In addition, the pacemaker 12 may have a further output and lead 21 coupled to a magnetically actuatable read switch 23 that may be actuated by the physician by bringing an external magnetic adjacent thereto to close the switch 23 to effect a change in the operation of the pacemaker 12. Lead 29 is illustrative of a plurality of leads that may be coupled to various sites of the patient's heart in order to provide, for example, stimulation that would defeat an arrhythmia or to provide redundant leads to replace a defective lead 17 or 19.

Figure 2:
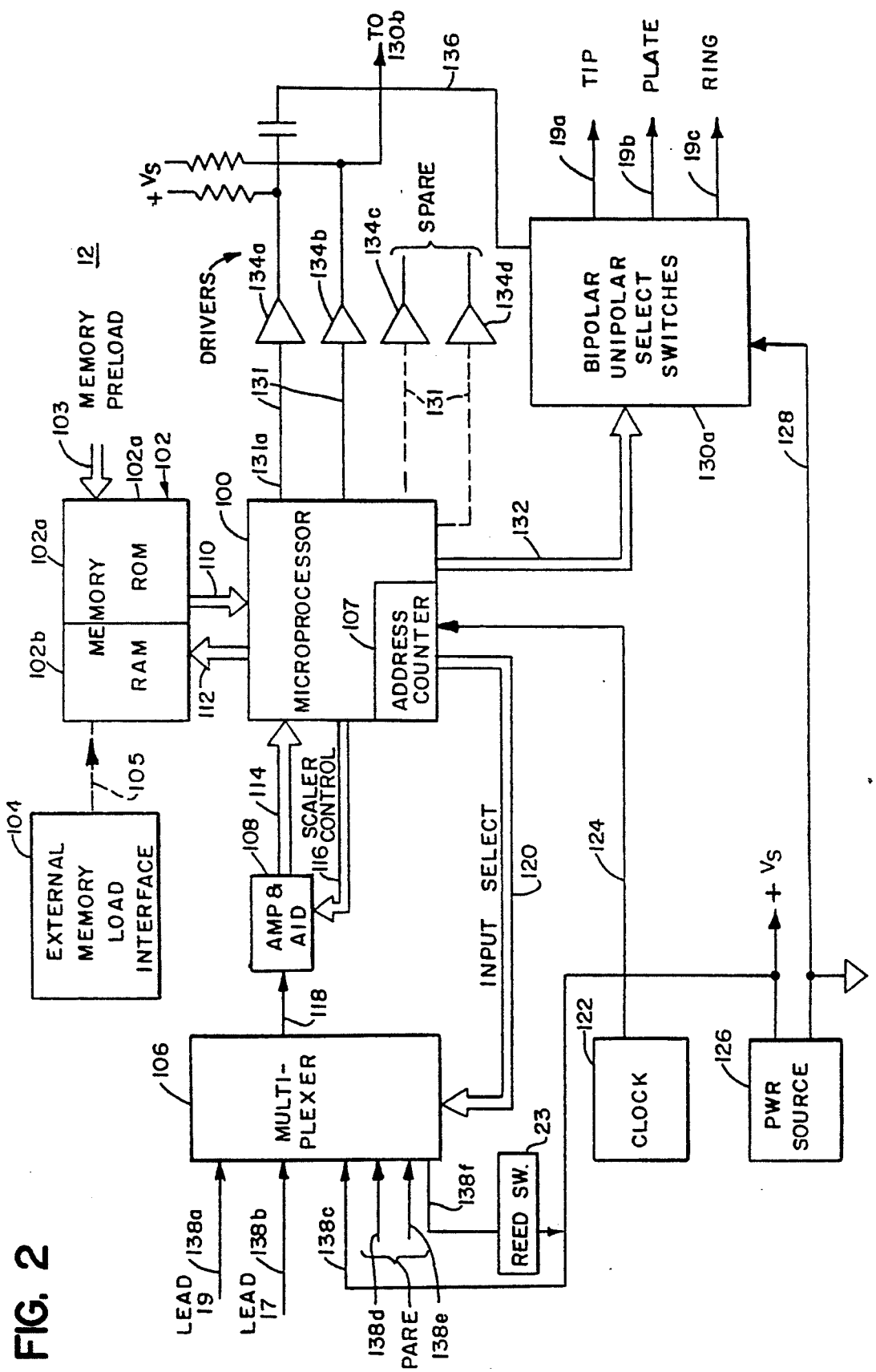
FIG. 2 is a functional block diagram of the internally implanted pacemaker, as generally shown in FIG. 1.

With reference to FIG. 2, there is shown a functional block diagram of the pacemaker 12, which includes as its central control element a microprocessor 100, and a multiplexer 106 for receiving analog data from a first input 138a coupled via the first lead 19 (see FIG. 1) to the patient's ventricle 42 and a second input 138b coupled via the second lead 17 to the patient's atrium 40 (see FIG. 1). These various analog (and digital) inputs are selected by the multiplexer 106 under the control of the microprocessor 100 in a selected manner and processed according to processes or programs stored in the memory 102.

In addition, the microprocessor 100 is coupled by an address bus 112 to memory 102, whereby addresses as stored and incremented by an address counter 107 are applied to address selected locations within the memory 102. The addressed data is transferred from the memory 102 via data bus 110 to the microprocessor 100.

In addition, there are additional inputs 138c, d, e and f of the multiplexer 106. The microprocessor 100 provides control signals via an input select bus 120 to the multiplexer 106, whereby one of the inputs 138a to f is selected for application via the conduit 118, a scaling amplifier and analog to digital (A/D) converter 108 and the bus 114 to the microprocessor 100. As suggested in FIG. 2, the output voltage $V_s$ of a power source 126 is coupled via input 138c to the multiplexer 106 in order to appropriately modify the pacer performance as a function of power source variations. For example, it is desired to increase the pacing pulse width as supply voltage decreases to create a more constant energy pulse, or to slow the pacing rate as supply voltage decreases to indicate a need for pacer replacement or modification via external programming. The spare inputs 138d and 138e may be coupled illustratively also to the ventricle 42 and the atrium 40 in order to redundantly sense the activities of these portions of the heart. It is contemplated that the microprocessor could choose which of the inputs 138a, b, d and e that would provide the most efficient sensing of the atrial and ventricular signals, or require the least power from the power source 126, or most effectively breakup a cardiac arrhythmia. Further, the input 138f may be connected by the lead 21 to the reed switch 23, whereby the physician may dispose an external magnet to close the switch 23, whereby the microprocessor 100 is controlled to change or alter the program as stored in the memory 102. The multiplexer sequentially selects or steers one of the inputs 138a to f via conduit 118, which is input through an amplifier and analog digital converter 100 and the conducter 114 to the microprocessor 100. Multiplexing is used in order to reduce the hardware required for processing the analog information applied to the inputs 138a to f and also to reduce the power requirements for this function. Without the multiplexer 106, each of the inputs 138a to f would require its own individual scaling, amplifier and A/D converter 108. Thus, the use of the multiplexer 106 reduces the power drain applied to the power source 126 as well as reduces the circuitry to be incorporated within the pacemaker 12.

The microprocessor 100 applies via conduit 116 a scaler control signal to the scaling amplifier and A/D converter 106, whereby the scaling factor or gain of the amplifier within block 108 is controlled to accommodate for the various amplitudes of signals applied to the inputs 138a to f of the multiplexer 106. In this regard, it is understood that the output of the power source 126 could be illustratively in the order of 1.3 to 6 volts (initially), whereas the heart activity signals derived from the atrium 40 and the ventricle 42 would be illustratively in the order of 1 to 20 millivolts. The output of the amplifier and A/D converter 108 is a set of digital signals that are to be stored within the microprocessor 100 and in particular within the registers of the microprocessor 100. In a preferred embodiment of this invention, the microprocessor 100 could also be implemented by presently available low threshold CMOS technology, which implementation would provide a relatively low power drain upon the power source 126.

An essential element of the pacemaker 12 is the memory 102 which may include a non-volatile section, i.e., the read-only memory (ROM) portion 102a and a volatile portion, i.e., the random access memory (RAM) portion 102b. In the ROM or non-volatile portion 102a, the basic steps of each of a variety of pacing modes (or other processes) are stored. On the other hand, a variety of parameters or whole programs are stored in the RAM portion 102b, and at a later point in time could be reprogrammed dependent upon the changing condition of the patient. The memory 102 may be programmed at the time of manufacture, before implantation within the body 14 of the patient, or via an external memory load interface 104, that is coupled by an RF frequency or acoustical link 105 to the memory 102. In an illustrative embodiment of this invention, a link as described in U.S. Pat. Nos. 3,833,005 and 4,066,086 (more fully identified above), may be readily adapted to be used as the interface 104. In particular, there is described a receiver filter for sensing bursts of RF pulses transmitted from an external transmitter, the bursts being coded in a manner to reprogram a program stored within the memory 102 or alternatively, to change a parameter stored within a memory location of the memory 102.

Thus, after the pacemaker 12 has been implanted within the body 14 of the patient, the physician upon observing a change in the patient's condition, may reprogram the program or specific variables of a program stored within the RAM portion 102b to most appropriately pace the patient's heart for his changed condition. Specifically, it is noted that there are various parameters of pacing such as the pulse width of the stimulating pulse, the rate or frequency of pulse application, the period between the application of a pulsing signal and the detection of the responsive heart activity during which the sensing apparatus is defeated, and the pulse amplitude. Typically, each of these parameters is determined by, for example, an eight bit word stored in a word location of the RAM portion 102b of the memory 102. Thus, if it is desired to change the pulse width, the physician may readily enter via the interface 104 and conduit 105 into a known, addressable word location within the RAM portion 102b, a new eight bit word indicative of the new pulse width at which the pacemaker 12 is desired to pace. It is contemplated that a new mode of pacing may likewise be programmed within the RAM portion 102b by inserting via the interface 104 the steps of the new process. Alternatively, a mode change may be effected by inserting the starting location of the desired program from the RAM portion 102b within address counter 107 of the microprocessor 100 to initiate the addressing of the next program within the ROM portion of memory 102. For example, if the initial mode of operation of the pacemaker 12 is ventricular demand pacing and it becomes desired to initiate an A-V sequential pacing mode, the physician enters the new starting address of the A-V sequential pacing mode via the interface 104 to access a different portion of the ROM portion 102a, whereby the microprocessor 100 initiates the operation of the next mode.

As will be explained in detail later, it is desired to maintain constant the energy of each stimulating pulse applied to the patient's heart, even though the voltage level of the power source 126, e.g., a battery, decreases with life. As indicated in FIG. 2, the multiplexer 106 periodically applies the battery voltage $V_s$ via the input 138c to the microprocessor 100, which under the control of a program stored in the memory 102 compares the measured voltage with various predetermined voltages stored in the ROM portion 102a or the RAM portion 102b whereby an adjustment in the pulse width of the stimulating pulse is made to maintain substantially constant the energy content, i.e., the area underneath the curve of the stimulating pulse.

Further, it is contemplated that the memory 102 may be loaded with a program that is in effect self-choosing. In other words, such a program could be responsive to the heart's signals as applied to the inputs 138a and b to sense the condition of the heart and to choose one of a plurality of programs dependent upon the sensed condition. The distinguishing characteristics of the atrial P wave and ventricular R wave input signals are more fully described in the publication, entitled "Electrocardial Electrograms and Pacemaker Sensing" by P. Hoezler, V. de Caprio and S. Furman and appearing in *Medical Instrumentation*, Vol. 10, No. 4, July, August, 1976. In this regard, the criteria with which these heart signals are to be recognized and compared, is stored within the memory 102 and if a change is noted, the microprocessor may automatically select a different mode of pacing appropriate for the changed conditions of that patient's heart without the need for external intervention by a physician through external memory lead interface 104.

In a further mode of pacing, it is contemplated that the memory 102 of the pacemaker 12 may be programmed to operate as an automatic threshold following pacemaker, whereby the energy of the stimulating pulses applied to the patient's ventricle 42 (or atrium 40) may be decreased incrementally until capture is lost, i.e., the stimulation pulses fail to elicit a responsive ventricular contraction evidenced by an R wave sensed within a sensing period. In this mode, if the R wave is sensed within the period, a control signal is developed to decrease the pulse energy level by a given incremental amount. In particular, the pulse width is decreased until no pacemaker elicited R wave is sensed at which time the program increases the pulse width until the R wave reappears. In this fashion, the power drain placed upon the power source 126 is minimized in that the pulse width is adjusted for a level just sufficient to maintain capture of the patient's heart.

Continuing with respect to FIG. 2, the control output signals of the microprocessor are applied via conduits collectively shown by numeral 131 to latch drivers 134 and by bus 132 to corresponding select switches 130, which provide appropriate pacemaker pulses via the leads 17 and 19 (or 29) to the atrium 40 and ventricle 42 of the patient's heart in accordance with the processes stored in the memory 102. In particular, conduit 131a is coupled to a first or ventricular driver (or amplifier) 134a, which is in turn coupled to its own set of bipolar-/unipolar select switches 130a. It is understood that each of the driver amplifiers 134b, c and d is also associated with a similar set of select switches. For example, the output of driver 134b is connected to select switches 130b for driving the patient's atrium via conduits 17a, 17b and 17c. It is also understood that the drivers 134a–134d may include voltage increase circuitry, e.g., doublens, triplers to raise the output voltage level to that necessary to effectively stimulate the heart tissue with a given power source voltage. The select switches 130 are under the control of signals derived from the microprocessor via bus 132 to selectively couple the output of the first driver 134a between selected of the outputs 19a, 19b, and 19c. In this regard it is understood that the switches 130 are coupled via the ventricular lead 19 which may take the form of a coaxial lead connected to a tip electrode via conducter 19a and to a ring electrode 19c, as more fully shown and explained, for example, in U.S. Pat. No. 4,010,758 by R. H. Rockland et al, as assigned to the assignee of this invention. In addition, there is provided a conductor 19b coupled to a plate formed of the metal container or can 13 in which the pacemaker 12 is encapsulated. In normal bipolar operation, the select switches 130 connect the negative and positive stimulating pulses via the conductors 19a and 19c of the coaxial lead to the tip and ring electrodes, respectively. If it is desired to pace in a standard unipolar mode, a negative voltage is applied via the conducter 19a to the tip electrode and a positive voltage via the conductor 19b to the plate, with the ring electrode not connected.

In addition to being able to pulse in bipolar or unipolar mode, it is desired to provide a fault tolerant pacemaker whereby if it is detected that there is a faulty lead due to an improper connection of an electrode lead to the heart tissue or to the breakage or damage of a lead, the microprocessor 100 responds to provide suitable control signals via the buss 132 to the select switches 130, whereby a different combination of leads (or conductors of leads) are selectively coupled to apply the pacing pulses to the ventricle 42. For example, the select switches 130 may be arranged to interconnect the tip and ring leads 19a and 19c together. Alternatively, the select switches 130 are selectively closed to apply the heart pulse between either one of the tip lead 19a or plate lead 19b and the ring lead 19c, whereby in the event of failure of one of the leads 19a or b that another could readily be used in its place and still apply the pulse across two sites of the patient's heart.

Failure of one of the leads 17 or 19 can be detected by loss of capture, i.e., failure to note a heart activity signal at the input 138b after the pacing of the ventricle. Alternatively, measuring a high impedance between the conduits 19a and 19b of the coaxial lead 19, indicates the failure of the lead due either to the build-up of scar tissue between one of the tip or ring electrodes and the ventricle 42, or the breaking of one of its conduits 19. Upon detection of such a failure, the microprocessor 100 selects a different one of the processes or programs stored within the memory 102 to apply signals to one of the select switches 130 to cause a re-connection of the leads 19a (or 29) in a manner as illustrated above.

An output of the microprocessor is also coupled to a second or atrial stimulating amplifier 134b whose output is coupled to a further set of select switches 130 to be coupled via a corresponding set of leads 17 to the patient's atrium 40, as shown in FIG. 1. In addition, there is included spare amplifiers 134c and 134d, which receive outputs of the microprocessor 100 and are coupled to further sets of select switches 130. It is contemplated that such sets of select switches 130 may be coupled by redundant leads to the patient's heart. For example, the outputs of the amplifiers 134c and 134d could also be coupled redundantly to the ventricle and atrium 42 and 40 of the patient's heart. If one of the leads 19 or 17 broke or the resistance between its electrode and the patient's heart became excessive, a redundant lead could be coupled in circuit between the microprocessor 100 and the patient's heart by appropriate activation of the corresponding set of select switches 130. To measure the impedance as presented by one of the leads 17 and 19, it is noted that such a lead is coupled to an output circuit, as will be described with respect to FIGS. 3, including a charging capacitor and that an indication of the charging time of such capacitor is an indication of the impedance presented by the associated lead. In operation, the output capacitor is charged, and after charging, the output circuit is actuated to effect a discharge of the capacitor whereby a stimulating pulse is applied via the associated lead to the patient's heart. It is contemplated that the period required to charge the output capacitor be timed, by initiating a counter effected by a program within the memory 102, the counting continuing until the charged voltage level upon the output capacitor reaches a predetermined level. Thus, the voltage level of the capacitor will be repeatedly measured under the control of the microprocessor 100 and if not above the predetermined level, the counting operation will continue. When the charged voltage of the capacitor has reached the predetermined level, the counting operation ceases and that count is used as an indication of the impedance of the lead. If the lead is open, the impedance of the lead will be high thereby causing the charging time period to be greater, whereas if the lead is shorted out, the time period will be relatively short. Thus, first and second time limits are established to determine whether the lead is shorted or its impedance is too high corresponding to a break of the lead. In either case, these limits, taking the form of time counts, are checked and if exceeded, a second, redundant lead is substituted for the defective one.

The spare drivers 134 may be provided in order to provide stimulation to a plurality of different sites, e.g., 5, in order to break up arrhythmias that may be sensed by the pacemaker 12. Alternatively, the additional drivers 134c and d may be used to discharge polarization voltage on the leads 17 and 19 after pacing or used quickly to charge the output capacitor for high rate pacemakers. Arrhythmias may be detected by measuring the delay between the electrical activity of a first heart site, e.g., the atrium, and the detection of heart activity at a second heart site, e.g., the ventricle. If the delay is less than a predetermined period, e.g., 100 to 200 milliseconds, there is an indication of a possible arrhythmia. Arrhythmias are primarily caused by the occurrence of a second competing ectopic focus within a patient's heart, that beats in competition with the primary focus typically occurring in the patient's atrium. The two centers of beating compete with each other to produce arrhythmia, whereby the heart's activity becomes erratic and does not pump blood efficiently. In an illustrative embodiment of this invention, it is contemplated that a plurality of electrodes, each coupled to an amplifier 134 and a select switch 130 is coupled to a corresponding number of selected sites of the patient's heart. One such lead is selected to apply stimulating pulses to the patient's heart, the remaining leads being coupled to sense the resultant heart activities at the remaining sites. Time windows are established by a program stored within the memory 102 for each of the four leads in which to receive heart activity signals and if the signals are not received within the time windows, there is an indication of possible arrhythmia. If a detected signal is not within its window, a different one of the plurality of leads is selected to apply the stimulating pulses, and the remaining leads sense the resultant heart activity signals. If the sensed signals do not appear within the timing windows, after the selection of the new stimulating lead, a different lead is then selected. If the arrhythmia is not brought under control by this action, the program is designed to apply stimulating pulses to all of the leads to bring the heart's activity under control. The timing periods in which to receive the heart activity signals, are established in a manner as explained below with respect to FIGS. 4 and 5.

It is evident by the above description, that the pacemaker 12 is an exceptionally flexible, adaptive device permitting correction or compensation for a variety of factors such as sensing difficulties, power source voltage variations with respect to time and unforeseen noise sources. For example, processes or programs are loaded into the memory 102 for sensing the R waves based upon such major features as the slope of the EKG signal, the pulse width of the R wave from the patient's ventricle 42, the amplitude of the R wave, the similarity of the R wave to a previous EKG complex, etc. In addition, the memory 102 is programmed to ignore extraneous AC noise sources or to ignore or to filter out extraneous muscle signals. The advantages of such an adaptable pacemaker 12 permit a single pacemaker to be provided that is capable of being programmed in a variety of operations and to be continuously reprogrammed as technology changes. From a manufacturing point of view, it is no longer necessary to modify each hardwire circuit to develop separate hybrid circuits which differ from each other by minor features for example, a change of the input filter, pulse width or pulse rate. A further advantage of the pacemaker 12 of FIG. 2 is that it eliminates the use of a major source of failure, i.e., the rate and pulse width timing capacitors within prior art, hardware implemented pacemakers. At present, hardwire pacemakers utilize a resistor/capacitor charging scheme to accomplish the desired timing functions, such as pulse width, pulse rate and refractory timing. Experience indicates that capacitors can be a major source of failure in such circuits.

In this embodiment of this invention, the microprocessor 100 may take the form of a processor as manufactured by RCA Corporation under their designation "CDP 1802 COSMAC" microprocessor or the "CDP 1804 COSMAC" microprocessor (processing on-chip memory).

Figure 3A:
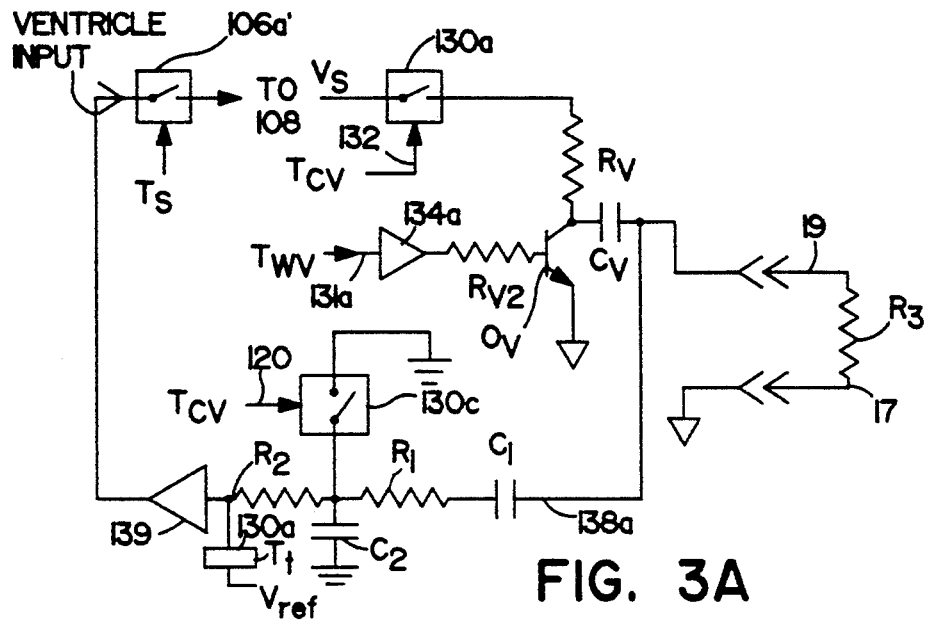
FIG. 3A shows a circuit diagram of the particular interconnections from the pacemaker of FIG. 2 to the patient's heart to implement a ventricular demand mode of pacing and sensing.

As explained above with respect to FIG. 2, each of the drivers 134 is connected to its own set of select switches 130, whereby a stimulating pulse is applied by one of the leads 17 or 19 to a corresponding part of the patient's heart. Additionally, the multiplexer 106 applies a selected signal derived by the leads 19 or 17 from the ventricle 42 and atrium 40 to the microprocessor 100. In FIG. 3A, there is shown an illustrative arrangement of driver amplifiers 134 and select switches 130 to apply the stimulating pulses via the lead 19 to the patient's ventricle 42 to effect a ventricular demand mode of pacing, the timing intervals of which are shown in FIG. 4A. The numerals used to designate elements of FIG. 3A correspond to those numerals as shown in FIG. 2 to designate like elements or blocks. In particular, a pacemaker output circuit is comprised of an output transistor $Q_V$ for coupling the voltage on capacitor $C_V$ selectively to the ventricle 42 via the lead 19. In particular, an output control signal $T_{WV}$ of the microprocessor 100 is coupled via conductor 131a, amplifier 134a, resistor $R_{V2}$ to the base of transistor $Q_V$, rendering it conductive. As a result, the previously charged capacitor $C_V$ is discharged to ground, applying a stimulating pulse of a pulse width corresponding to that of signal $T_{WV}$, via lead 19 to the patient's ventricle 42. The select switch 130a is closed for a selected period by the control signal $T_{CV}$ applied via bus 132 to recharge the capacitor $C_V$ in the interval between successive control signals $T_{WV}$. Thus, the control signal $T_{WV}$ selectively renders the transistor $Q_V$ conductive and nonconductive whereby corresponding series of stimulating pulses are applied via the lead 19 to the patient's ventricle 42. In the unipolar pacing mode, the plate or container 13 of the pacemaker 12 is connected to the other terminal of the battery.

As shown in FIG. 3A, the ventricular lead 19 is also connected via conductor 138a to the multiplexer and in particular to a switch 106a', which is closed in response to the timing window signal $T_S$ thereby applying a signal indicative of the heart's ventricular activity via the amplifying and A/D circuit 108 to the microprocessor 100. In particular, the ventricular lead 19 is coupled via the conductor 138a, the capacitor C1, the resistors R1 and R2 and amplifier 139 to the multiplex switch 106a'. In comparing the functional block diagram of FIG. 2 and the circuitry of FIG. 3A (and FIGS. 3B and C), it should be noted that there is not a precise correspondence between the elements of these figures. Though it is indicated that certain switches notably switch 106a' is a part of the multiplexer 106, there is a difference in the circuits in that the circuit of FIG. 3A (and 3B and C) includes sense amplifiers, e.g., ventricular sense amplifier 139, whereas the multiplexer 106 of FIG. 2 applies a selected one of a plurality of analog inputs to a single amplifier 108. Thus, it is contemplated that the various switching functions shown illustratively in FIG. 3A (and FIGS. 3B and C) are illustratively shown therein and could be implemented in varying manners; for example, the multiplex switch 106a' could be implemented by a select switch 130. The point of interconnection between the resistor R2 and R1 is coupled to ground via capacitor C2. As will be noted with respect to FIG. 4A, it is desired to clamp the amplifier 139 to ground during certain periods, i.e., the refractory period, in which it is not desired to sense the ventricular signal. To this end, a timing signal $T_{CV}$ is applied via the conductor 120 to a select switch 130c, whereby the point of interconnection between the resistors R2 and R1 is coupled to ground for the refractory period. The circuit formed of resistors R1 and R2, and capacitors C1 and C2 serves as a coupling circuit between the ventricular sensing amplifier 139 and the patient's heart. In particular, when the multiplex switch 106a' is closed coupling the input of the ventricular sensing amplifier 139 to ground, it is desired to provide isolation between ground and the patient's heart, otherwise significant damage could be caused to the patient's heart. To this end, resistor R1 and capacitor C1 are inserted between ground and the patient's heart. In addition, capacitor C2 functions as a low pass filter of noise that may be present upon the lead 19, as well as to soften the closing action of the select switch 130c. It is contemplated that the ventricular sensing amplifier 139 may take the form of a well known operational amplifier, and resistor R2 is coupled to its input in order to set its gain in a manner well known in the art.

In FIG. 4A, there is shown a timing diagram of the ventricular demand pacing mode corresponding to the output/input connections of FIG. 3A, by which the system of FIG. 2 is adapted to pace the patient's ventricle 42. At time $t_0$, a ventricular pacing pulse has just been applied via lead 19 to the patient's ventricle 42. Thereafter, the RV or ventricular sensing amplifier 139 is clamped to ground by closing the select switch 130c for the refractory period from $t_0$ to $t_1$. Also during the refractory period, the capacitor $C_V$ is recharged by applying the control signal $T_{CV}$ to close the select switch 130a, whereby the potential of $V_s$ is applied to and recharges the capacitor $C_V$. Typically, the refractory period is in the order of 325 milliseconds at the time the pacemaker 12 is implanted within the patient and the battery or potential power source 126 is fresh. During the refractory period, the heart activity of the ventricle 42 is not sensed in that various noise or extraneous electrical signals may be present within the ventricle 42 that are not desired to be sensed. After the refractory period beginning at time $t_1$, the select switch 130c is opened and the switch 106a' is closed, whereby if the heart generates an R wave signal that would be applied via lead 19, conducter 138a, the ventricular amplifier 139 and the closed switch 106a', the microprocessor 100 responds by resetting the timing cycle to $t_0$. The occurrence of the R wave signal from the ventricle 42, indicates that the heart activity is normal and that it is not desired to apply a competing stimulating ventricular signal. Thus, as long as the patient's heart generates an R wave signal, the pacemaker 12 will not generate a ventricular pacing signal. However, if after the expiration of the sensing period from $t_1$ to $t_2$ without sensing an R wave, the microprocessor 100 will generate a timing signal $T_{WV}$ that is applied via conductor 131a, amplifier 134a, resistor $R_{V2}$ to the base of transistor $Q_V$, whereby the transistor $Q_V$ is rendered conductive causing the capacitor $C_V$ to rapidly discharge through the heart load (represented by resistance $R_3$) thereby causing a pacing pulse to be applied via leads 19 and 13 to the ventricle 42. During the pacing period from $t_2$ to $t_3$, the ventricular amplifier 139 is clamped to ground by the closed switch 130c. It is understood from the above discussion that the various periods corresponding to the pulse width of the ventricular pulse between times $t_2$ and $t_3$, the refractory period between $t_0$ and $t_1$ may be adjusted or reprogrammed by entering new eight bit words into the memory 102, as shown in FIG. 2.

Figure 4C:
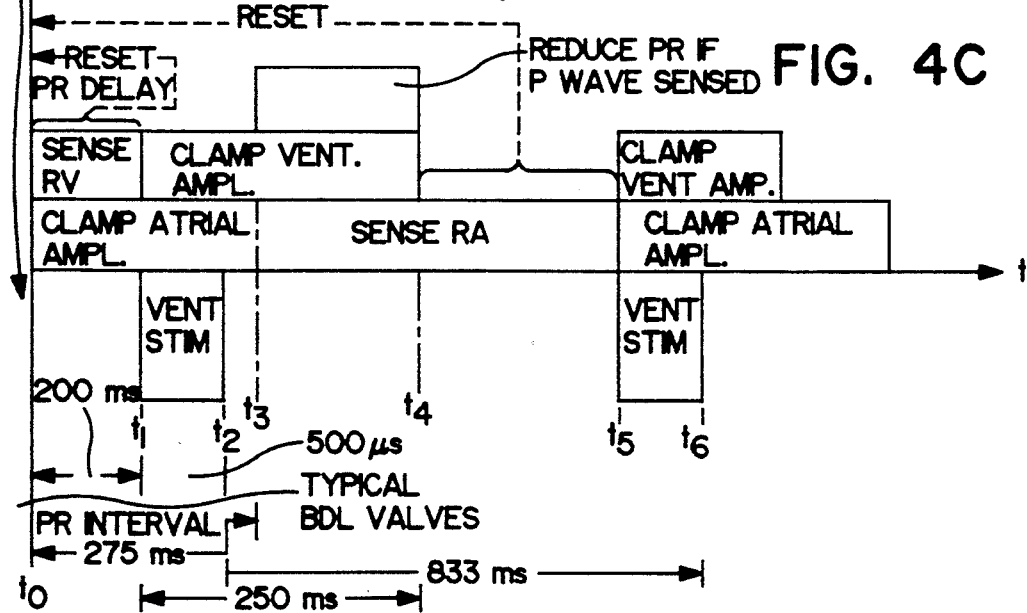
FIG. 4C is a timing diagram of the actuation of the switches and elements of FIG. 3C to implement an ASVIP mode.
Figure 4A:
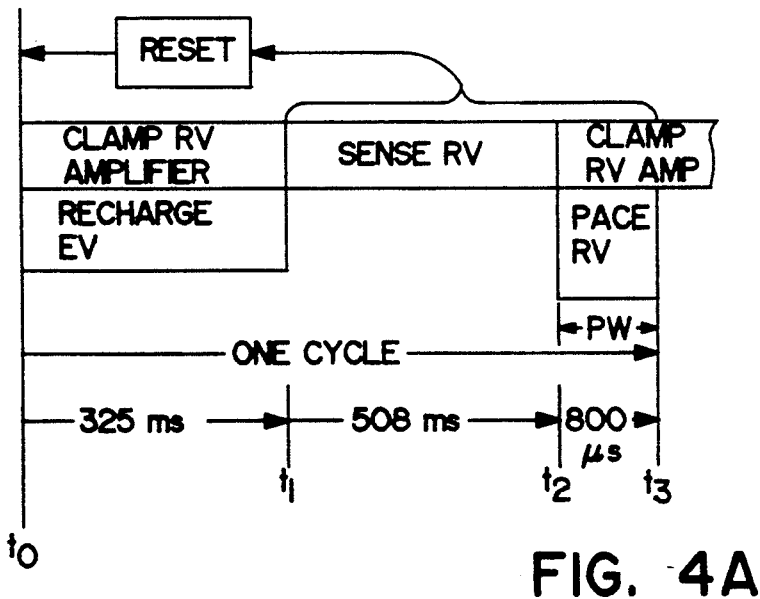
FIG. 4A is a timing diagram of the activation of the switches and elements of the circuit of FIG. 3A to implement a ventricular demand pacing mode.
Figure 5:
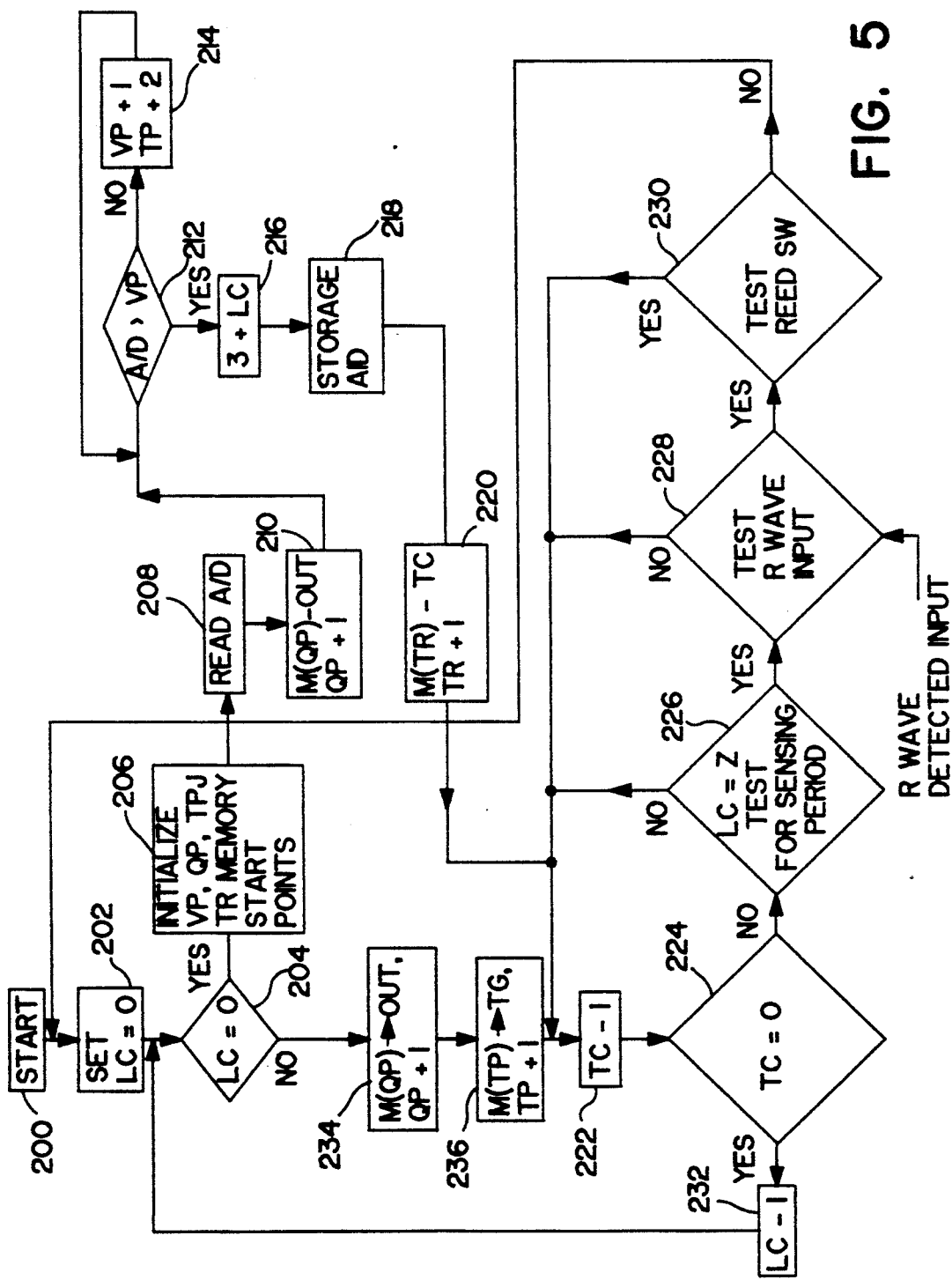
FIG. 5 is a flow diagram of one of a plurality of programs to be stored within the memory of the pacemaker shown in FIG. 2, to implement a ventricular demand mode of pacing in accordance with the timing diagram of FIG. 4A.

There is shown in FIG. 5 a flow diagram of the steps for implementing ventricular pacing in a demand mode, the timing diagram of which is shown in FIG. 4A, and the output and input circuit connections are shown in FIG. 3A to the pacemaker 12 as shown in FIG. 2. In one illustrative embodiment of this invention, the microprocessor 100 includes a plurality of pointer registers for storing pointers or addresses to word locations within the ROM portion 102b of the memory 102. In this illustrative embodiment, there are included within the microprocessor 100 the following registers for storing the indicated pointers or addresses:

R(0)=Program Counter (PC)
R(3)=Loop Counter (LC)
R(4)=Time Counter (TC)
R(A)=Output State Table Pointer (QP)
R(B)=Time Duration Table Pointer (TP)
R(C)=Voltage Transition Point Table Pointer (VP)
R(D)=Refractory Time Pointer (TR)
R(E)=Input Pointer (VDD).

Further, the flag inputs for the reed switch (EF2) and the R wave (EF1) are applied to the microprocessor as will be explained with regard to FIGS. 7A and 7B. The notation for the flag inputs and the pointers and counters is used throughout the program listing set out below. As is conventional with microprocessors, the microprocessor 100 includes the address counter 107 which increments one for each step of the program as it is carried out under the control of the microprocessor 100 to designate the next location within the memory 102 from which information is to be read out. The steps to be explained with respect to FIG. 5 to effect a ventricular demand mode of pacing, were implemented in an RCA COSMAC microprocessor by the following machine instructions:

| Memory Address (Hexadecimal) | Symbolic Notations | Memory Contents (Hexadecimal) | Remarks | Step Location |
|---|---|---|---|---|
| 00 | 0000 | D = 00 | | 200 |
| 01 | LDI | F8 | } Set LC = 0 | 202 |
| 02 | 00 | 00 | | 202 |
| 03 | PHI, 3 | B3 | | 202 |
| 04 | PLO, 3 | A3 | | 202 |
| 05 | GLO, 3 | 83 | R(3)→D | 204 |
| 06 | BNZ | 3A | Is LC = 00 | 204 |
| 07 | OUTPUT | 3D | No? Go to OUTPUT | 204 |

-continued

| | | | | |
|---|---|---|---|---|
| 08 | LDI | F8 | State Memory Address 3D YES? SET OUTPUT State Table to Address A0 | 206 |
| 09 | QP | A0 | R(A) = QP | 206 |
| 0A | PLO, A | AA | | 206 |
| 0B | LDI | F8 | SET R(B)=TP206 | 206 |
| 0C | TP | A4 | | 206 |
| 0D | PLO, B | AB | | 206 |
| 0E | LDI | F8 | Set R(C) =VP | 206 |
| 0F | VP | B0 | | 206 |
| 10 | PLO, C | AC | | 206 |
| 11 | LDI | F8 | Set R(D) =TR | 206 |
| 12 | TR | A3 | | 206 |
| 13 | PLO, D | AD | | 206 |
| 14 | LDI | F8 | Set R(E) =VDD | 206 |
| 15 | VDD | B6 | | 206 |
| 16 | PLO, E | AE | | 206 |
| 17 | SEX, E | EE | Set X=E | 208 |
| 18 | INP | 68 | READ A-D 11($V_{DD}$) | 208 |
| 19 | SEX, A | EA | Set X=A | 210 |
| 1A | OUT | 60 | M(QP)→OUT, PQ + 1 | 210 |
| 1B | INC B | 1B | TP + 2 | 214 |
| 1C | INC B | B | | 214 |
| 1D | LDA, C | 4C | M(R(C))→D, VP + 1 | 214 |
| 1E | SEX, E | EE | E→X | 212 |
| 1F | SM | F7 | VP − VDD | 212 |
| 20 | BDF | 33 | If DF=1 VP≦VDD | 212 |
| 21 | VPVDDCompare | 1B | BRANCH to VPVDD Compare | 214 |
| 22 | DEC B | 2B | DECREMENT R(B) BY2 | 212,214 |
| 23 | DEC B | 2B | | |
| 24 | DEC C | 2C | DECREMENT R(C) BY1 | 212,214 |
| 25 | LDI | F8 | SET LC=3 | 216 |
| 26 | 03 | 03 | | 216 |
| 27 | PLO, 3 | A3 | | 216 |
| 28 | STROBE A-D | 62 (15) | | 218 |
| 29 | LDA, D | 4D | M(TR)→D, TR + 1 | 220 |
| 2A | PLO, 4 | A4 | M(TR)→TC | 220 |
| 2B | DEC, 4 | 24 | TC − 1 | 238 |
| 2C | GLO, 4 | 84 | | |
| 2D | BNZ | 3A | TEST TC=0 | 224 |
| 2E | TEST 2 | 32 | No.→to test LC = 2 | 224 |
| 2F | DEC, 3 | 23 | Yes, LC-1 | 232 |
| 30 | BR | 30 | | 232 |
| 31 | CHECK 0 (LC = 0) | 05 | | 232 |
| 32 | GLO, 3 | 83 | R(3)→D | 226 |
| 33 | XRI | FB | | 226 |
| 34 | 02 | 02 | Is LC=2 | 226 |
| 35 | BNZ | 3A | | 226 |
| 36 | DECTC | 2B | LC=2, BRANCH | 226 |
| 37 | BN1 | 3C | TEST R-Wave INPUT | 228 |
| 38 | DECTC | 2B | No R-Wave INPUT BRANCH | 228 |
| 39 | B2 | 35 | TEST REED SWITCH | 230 |
| 3A | DECTC | 2B | YES to DECREMENT TC | 230 |
| 3B | BR | 30 | No REED SWITCH | 230 |
| 3C | STRT-1 | 01 | BRANCH to STRT-1 | |
| 3D | SEX, A | EA | SET X=A,QP | 234 |
| 3E | OUT | 60 | M(QP)→OUT, QP + 1 | 234 |

-continued

| Address | Comment | Comment/Assembly Language | Machine Language Code | | |
|---|---|---|---|---|---|
| 3F | | LDA | 4B | | 236 |
| 40 | | PLO, 4 | A4 | M(TP)→TC, TP + 1 | 236 |
| 41 | | BR | 30 | BRANCH TO | 222 |
| 42 | | DECTC | 2B | DECREMENT TC | 222 |

| Address | Comment | Comment/Assembly Language | Machine Language Code |
|---|---|---|---|
| A0 | QP | Q REF | 01 |
| A1 | | Q PP | 02 |
| A2 | | P PW | 04 |
| A3 | TR | T REF | FF |
| A4 | TP | SP 5.2 V | 60 |
| A5 | | PW 5.2 V | 03 |
| A6 | | SP 4.8 V | 60 |
| A7 | | PW 4.8 V | 06 |
| A8 | | SP 4.4 V | 60 |
| A9 | | PW 4.4 V | 08 |
| AA | | SP 4 V | 60 |
| AB | | PW 4 V | 10 |
| AC | | SP 3.6 V | 60 |
| AD | | PW 3.6 V | 12 |
| AE | | SP 0 V | 60 |
| AF | | PW 0 V | 12 |
| B0 | VP | V 5.2 | 52 |
| B1 | | V 4.8 | 48 |
| B2 | | V 4.4 | 44 |
| B3 | | V 4.0 | 40 |
| B4 | | V 3.6 | 36 |
| B5 | | V 0.0 | 00 |
| B6 | VDD | | |

SP = Sense Period
PW = Pulse Width

In FIG. 5, there is shown a flow chart of the steps representing the instructions listed above, the corresponding step for its instructions being identified under the heading "Step Location". The program begins at the start step 200, transferring to step 202 wherein the loop counter LC formed by the register R(3), is set to zero as implemented by the instruction stored at the memory address 04, as shown above. The loop counter LC is part of a control means for determining which mode or period in which the pacemaker is operative as when it is pacing in a demand inhibited mode; in particular, the loop counter LC provides an output in the form of a binary number indicative of that state. As shown in FIG. 4A, the demand ventricular pacing mode includes a refractory state corresponding to the refractory period, during which the ventricular amplifier 139 is clamped, a sensing period state during which the electrical activity of the ventricles is accessed and sensed, and a pulse width state during which the ventricular stimulating pulse is applied to the patient's ventricle 42. As will be evident from a further description of the steps of the program, the program proceeds in loop fashion through the steps of FIG. 5 three times, once for each of the three mentioned states, with the loop counter LC being decremented upon completion of each loop to indicate that the process has moved to the next state.

Initially, the loop counter LC is set to zero in step 204. The process now moves to step 206, wherein the points VP, QP, TP, and TR as defined above are initialized to their starting points. For example, VP, as defined above, is the voltage transition table pointer. Thus, in step 206, the register R(C) is set to the first location within the transition point table, which defines the voltages with which the output voltage $V_s$ of the power source 126 is to be compared. The register R(C) is a part of the system's memory and the step 212 provides means for comparing the voltage $V_{DD}$ with one of the discrete voltage levels as stored within the register R(C). The pointer QP pointing to the output state table as stored in register R(A), points to that location within the output state table identifying which of the states as shown in FIG. 4A, the processor is, i.e., within either of the refractory period, the sensing or partial period or the pulsing or pulse width period. The output state table is reproduced below as follows:

| | | |
|---|---|---|
| Q11 | 01 | Refractory State |
| Q21 | 02 | Sense State |
| Q31 | 04 | Pulse Width State |

Next, in step 208, the microprocessor 100 commands the A/D converter 108 to read out a digital indication of the power source voltage $V_s$. In step 210, the output state QP as stored within the microprocessor register R(A) is incremented by one, i.e., to move it to the next output state. Thus, at this point, the register R(A) indicates that the process is in the initial refractory period. Next in step 212, the voltage $V_s$ is compared with the transition point voltage (VP) as pointed to by the voltage transition point table pointer VP as stored in register R(C). If the voltage $V_s$ is greater than the voltage transition point, the process moves to step 216; if not, the process moves to step 214, wherein the voltage transition point table pointer VP is incremented one to point to the next location therein to obtain the next lower value of the transition point voltage and further the time duration table pointer TP is incremented by two to designate the next two locations within the time duration table. The time duration table is stored within a designated location within memory means taking the form of the memory 102 as shown in FIG. 2.

The next value of the voltage transition point is obtained from the voltage transition point table, which is reproduced below as follows:

|    | HEX |              |
|----|-----|--------------|
| V1 | B3  | 179 = 5.2 V  |
| V2 | A2  | 162 = 4.8 V  |
| V3 | 91  | 145 = 4.4 V  |
| V4 | 80  | 128 = 4.0 V  |
| V5 | 6E  | 110 = 3.6 V  |
| V6 | 00  | = 0.0 v      |

The next set of values of the sense time and the pulse width are obtained from the time duration table which is set out below:

| T21 | 475 ms  | } $V_s \geq 5.2$ V |
| T31 | 800 μs  |                    |
| T22 | 475 ms  | } $V_s \geq 4.8$ V |
| T32 | 1000 μs |                    |
| T23 | 475 ms  | } $V_s \geq 4.4$ V |
| T33 | 1250 μs |                    |
| T24 | 475 ms  | } $V_s \geq 4.0$ V |
| T34 | 1550 μs |                    |
| T25 | 600 ms  | } $V_s \geq 3.8$ V |
| T35 | 1850 μs |                    |
| T26 | 600 ms  | } $V_s \geq 3.6$ V |
| T36 | 2300 μs |                    |

As seen in each two locations, there is given first a duration for the sense period and then the pulse width for a given voltage transition point, i.e., a reference value with which the voltage $V_s$ is to be compared. Thus, as will be explained, the program adjusts the pulse width of the ventricular stimulating pulse to maintain constant energy within the ventricular stimulating pulse, as well as to increase the sense period abruptly, as the voltage $V_s$ of the power source 122 attenuates, to provide a step rate slow down performance at end of battery life.

In step 214, the voltage transition point is moved from V1 to V2, e.g., from 5.2 to 4.8 volts. Again, the value of $V_s$ is compared with the voltage transition point (VP) and if greater (yes), the program moves to step 216 wherein the value of the loop counter LC is loaded with the value "three" indicating that the oscillator is in the refractory period. Thereafter, the A/D converter 108 is strobed in step 218 to read out the power source voltage $V_s$. In step 220, the value TR of the refractory period stored at location TR is read out and stored in the time counter TC (register R(4)). Step 218 provides means for sensing the voltage of the energizing source or battery for the pacemaker, and step 220 provides means responsive to the state in which the pacemaker is operative as well as the sensed voltage level of the energy source to select a count from the memory, i.e., the location TR, and to store it within a counter means as formed by the counter TC.

Thereafter, the process moves to step 222, wherein the value stored in the time counter (TC) is decremented by one and the timing of a period is initiated to cycle through step 222 until the value stored in the time counter (TC) is counted down to zero. The time counter TC comprises a counter means that is counted down by a clock means in the form of the clock 122 as shown in FIG. 2 as indicated by step 222. Next, in step 224, a decision is made whether the value of the time counter TC equals zero, i.e., its timing function has been completed, and if not, the process moves to step 226, where a decision is made to determine whether the loop counter LC equals to 2 indicating whether the process is in the sense state corresponding to the RV sensing period; if not, which is the case at the present point, the process loops through steps 222, 224, 226 until the initial count (corresponding to the refractory period) as set in the time counter TC has been decremented by step 222 to zero, as detected by step 224, thus terminating the refractory period. At that point, step 224 moves the process to step 232, wherein the loop counter LC is decremented by one, to thereby indicate that the process is in the sense state, i.e., LC equals 2, whereby the process returns to step 204. At this point, the loop counter LC does not equal to zero and the process moves to step 234, wherein the output state table pointer QP is incremented by one, whereat at this point in time, the process is moved to the sense state. Next in step 236, the value obtained from the time duration table is placed into the time counter TC, and the time duration table pointer (TP) is incremented by one to address the next wider pulse width within the time duration table.

Thereafter, the process moves via step 222 to decrement by one the count loaded into the time counter TC and if not zero as decided by step 224, the program advances to step 226 and if in the sense state, which the process is at this instance, the process moves to decision step 228 to determine whether an R wave has been applied to the multiplexer 106. If within the time period of a single decrement count, the R wave is not sensed, the process moves back to cycle to again, decrementing in step 222 the count corresponding to the sense period until the count equals zero as detected by step 224. If an R wave is detected by step 228, the process moves to step 230 to check the status of the reed switch 23 and if open, the process is reset as indicated in FIG. 4A to return the process to t0, i.e., to step 202 whereat the loop counter LC is reset to zero and the process is reinitialized. The reed switch 23 is a magnetically actuatable switch within the pacemaker 12. After implantation, the physician may actuate the reed switch 23 by placing an external magnetic close to the implanted pacemaker 12 whereby the reed switch 23 is closed to initiate the asynchronous mode of operation. If the reed switch 23 is closed indicating a desire to operate in the asynchronous mode, the process continues to loop, returning to step 222 to again decrement the time count TC, even if an R wave is detected. In this manner, the detection of an R wave is ignored and the pacemaker 12 proceeds to pace in the asynchronous mode of operation, without resetting upon detection of the R wave.

After the second sensing period has timed out, i.e., when the count stored in the time counter TC has counted down to zero as indicated by step 224, the process is again transferred to step 232 wherein the loop counter LC is decremented by one, wherein the value stored therein equals one indicating that the process is going into its third loop and is returning to step 204. Since the loop counter LC does not equal zero, the process transfers to step 234, whereby the value QP of the output state is incremented by one indicating that the process is now in the pulse width state. Next, in step 236, the value of the time duration is addressed and accessed from the time duration table and is stored in the time counter TC. The value of the time duration table pointer TP is incremented by one to point to the next location within the time duration table as set out above. At this point, the process enters into a series of cycles whereby the count within the time counter TC is decremented by one by step 222, and if not zero transfers to step 226 and not being in the sensing period, returns to be again decremented in step 222. The process repeats until the value of the count in the time counter TC has been decremented to zero as decided by step 224. At this time, the process again moves to step 232 wherein the loop counter LC is again decremented by one, the value now being zero. The process moves to step 204 and the process begins all over again with the initialization of the values of VP, QP, TP and TR by step 206.

In the above, there has been described the manner in which the pacemaker 12 implements the program for the demand ventricular mode as stored in the memory 102, moving first to the refractory period, then to the sense period and finally to the pacing or pulse width period before again beginning a new cycle. As indicated above, the length of each of the sense and pulse width periods is determined by the voltage $V_s$ of the power source 226, with the aforementioned periods and in particular the pulse width period increasing as the voltage $V_s$ decreases in order to maintain substantially constant the energy content of the ventricular stimulating pulse.

Figure 3B:
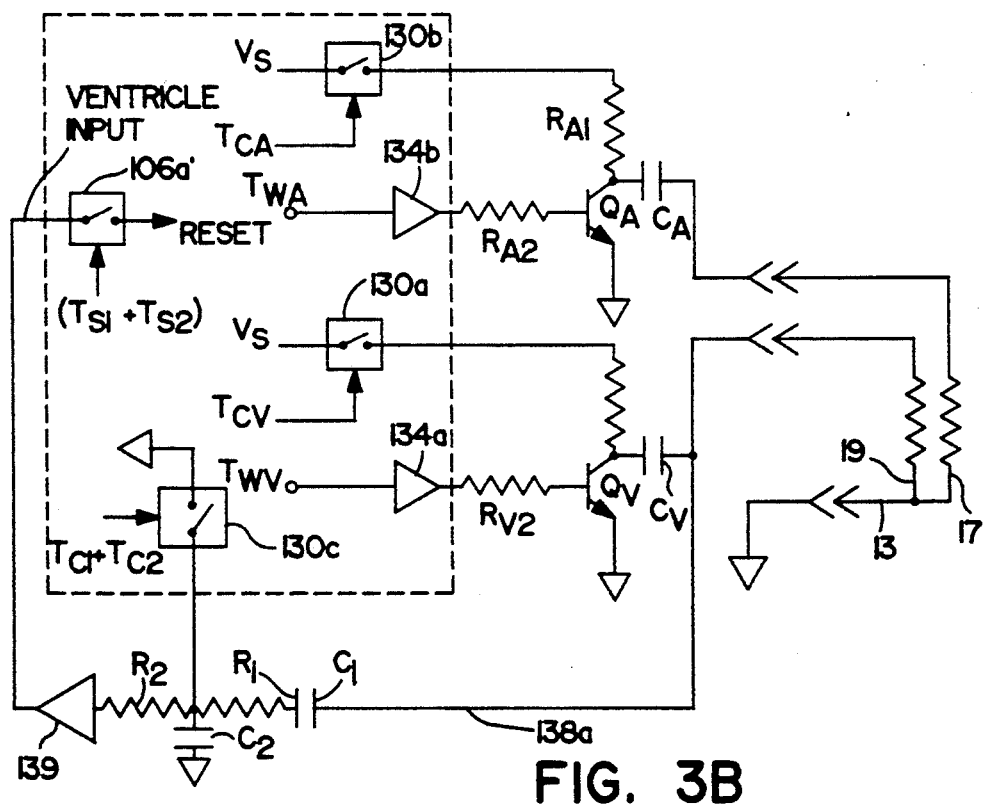
FIG. 3B is a circuit diagram showing the interconnections from the pacemaker of FIG. 2 to the patient's heart to implement an A-V sequential pacing of the patient's atrium and ventricle.
Figure 3C:
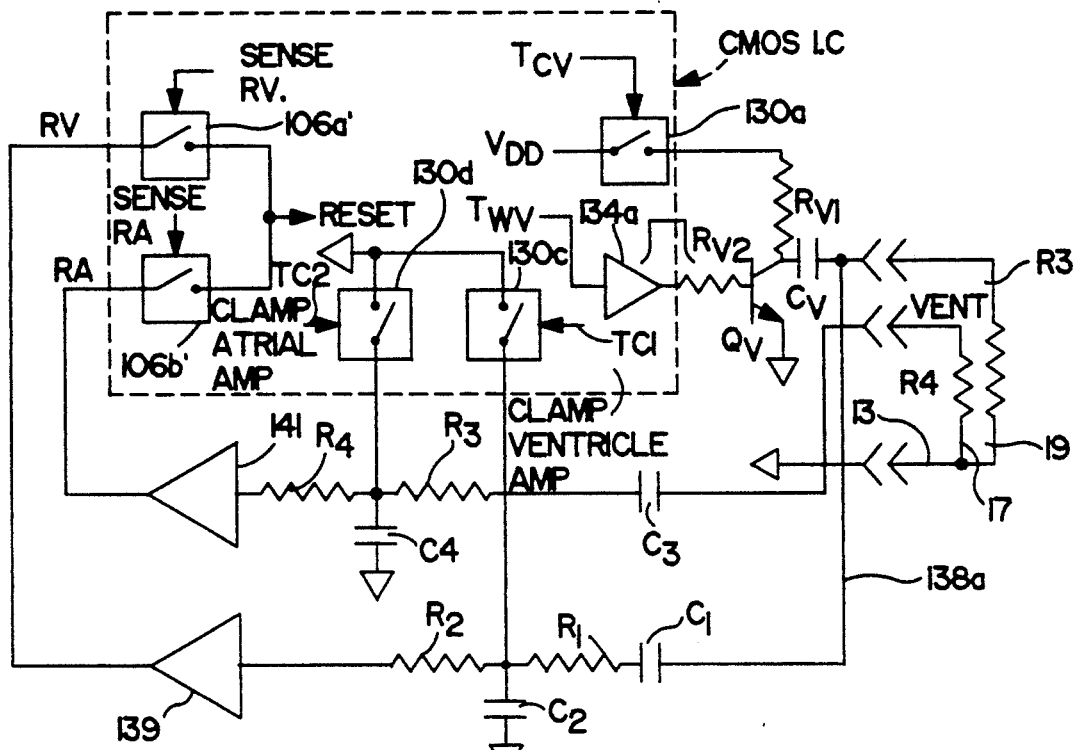
FIG. 3C is a circuit diagram of the interconnection from the pacemaker of FIG. 2 to the patient's atrium and ventricle to implement an atrial, synchronous, ventricular inhibited pacing (ASVIP) mode.

As explained, above, the memory 102 may be programmed with any of a plurality of modes of operation for pacing the patient's heart, selectably dependent upon the patient's condition, even a change of condition after the implantation of the heart pacemaker 12. For example as shown in FIG. 4B, the pacemaker 12 may be operated in an A-V sequential timing mode, wherein stimulating pulses are applied to each of the patient's ventricle 42 and atrium 40; after corresponding refractory periods the activity of the ventricle is sensed and if a ventricular signal does occur after either the stimulation of the ventricle or the atrium, the pacer is reset. The output and input connections of the pacemaker 12 shown in FIG. 2, are selected as shown in FIG. 3B. With respect to FIGS. 3B and 4B, the patient's ventricle 42 is pulsed immediately before time $t_0$ by applying a stimulus signal via the lead 19. After $t_0$, the ventricular sensing amplifier 139 is clamped by the application of the signal TC1 to the select switch 130c, whereby the input of the amplifier 139 is connected to ground for a first refractory period from $t_0$ to $t_1$. Also during the first refractory period, the ventricular output capacitor $C_V$ is recharged by applying the control signal $T_{CV}$ to the select switch 130a, whereby the power source voltage $V_s$ is applied to charge the capacitor $C_V$. In the period $t_1$ to $t_2$, a control or timing signal $T_{SI}$ as derived from the microprocessor 100 is applied to close the switch 106a', whereby a ventricular R wave, if present, is applied via the ventricular amplifier 139 and the multiplexer 106 to reset the timing operations of the microprocessor 100.

If at $t_2$ no ventricular R wave has been sensed, the pacemaker 12 causes a stimulating pulse to be applied via the lead 17 to the patient's atrium 40. In particular, a pulse control signal $T_{WA}$ is applied via the driver amplifier 134b and resistor $R_{A2}$ to the base of the output atrial transistor $Q_A$, rendering the transistor $Q_A$ conductive causing a discharge of the output atrial capacitor $C_A$ into and thereby stimulating the patient's atrium 40. Beginning at time $t_2$, the timing control signal is applied to select switch 130c, clamping the input of the ventricular amplifier 139 to ground, whereby any signal in response to the stimulation of the atrium is disregarded. Beginning at time $t_3$, the atrial output capacitor $C_A$ is recharged by the application of the timing control signal $T_{CA}$ to close the select switch 130b to apply the power source voltage $V_s$ to the capacitor $C_A$. In the period from $t_4$ to $t_5$, again the activity of the ventricle is sensed and a timing control signal from the microprocessor 100 applied to close switch 106a' permitting the ventricular R wave to be applied via the unclamped, ventricular amplifier 139 and the closed switch 106a' to the microprocessor 100. If the ventricular R wave is sensed during this second sensing period from $t_4$ to $t_5$, the timing period is reset to $t_0$. If no R wave appears in the period from $t_4$ to $t_5$, a timing pulse $V_{WV}$ is applied from the microprocessor 100 via the ventricular driver 134a and the resistor $R_{V2}$ to render conductive the ventricular output transistor $Q_V$, whereby the charged capacitor $C_V$ is coupled to ground discharging the capacitor $C_V$ and applying via the lead 19 a stimulating pulse to the patient's ventricle 42. Typical values for the periods TA extending from T0 to T2 and for the period TV from T0 to T5 are provided below:

| TV(MS) | TA(MS) |
|--------|--------|
| 2000   | 1700   |
| 1000   | 750    |
| 850    | 700    |
| 850    | 650    |
| 750    | 600    |
| 750    | 500    |
| 650    | 300    |
| 550    | 425    |

The A-V sequential method of operation as shown in FIG. 4B may be programmed illustratively in a manner similar to that shown in FIG. 5, except that the six output states and their corresponding time periods as shown in FIG. 4B, are set by counter values as derived from a corresponding table stored in the memory 102. Thus initially, typical values of TV and TA are programmed for a particular patient by accessing particular locations within the corresponding tables, one for each of the six periods. After a count has been entered into the time counter, successive cycles are carried out until the count is counted down to zero to time out that period.

Figure 4B:
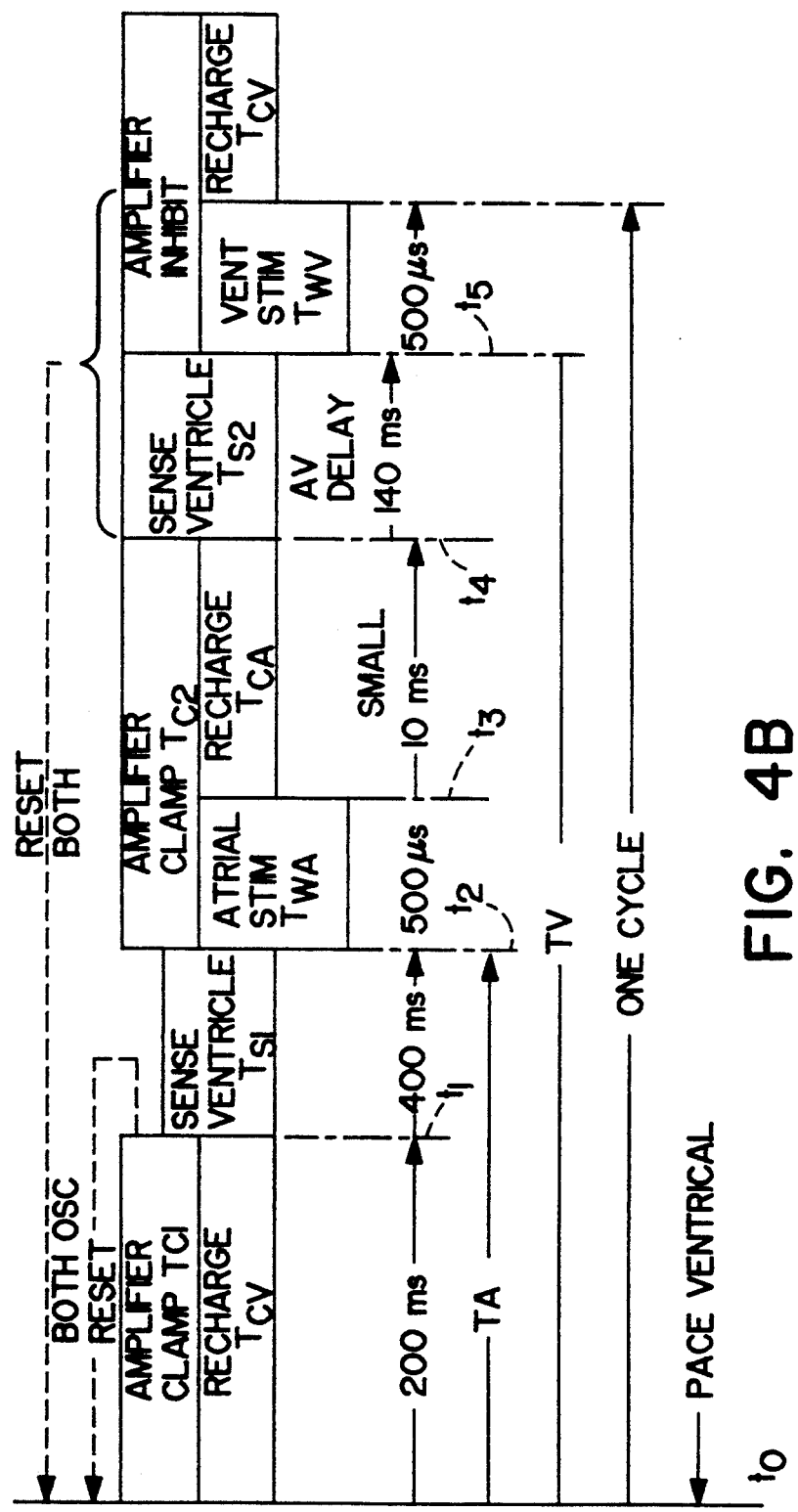
FIG. 4B is a timing diagram of the actuation of the switches and elements of FIG. 3B to implement a bifocal pacing mode.

In FIG. 4C, there is illustrated the timing diagram of an atrial synchronous ventricular inhibited pacemaker (ASVIP), wherein each of the ventricular and atrial activity of the patient's heart is sensed to reset the timing period. Such a mode of operation is typically used in a younger patient whose atria are beating in a normal fashion but whose ventricles may or may not be defective. It is desired to speed up the beating of the atria and to stimulate thereby the ventricular activity. A sensed atrial P wave initiates a timing cycle; however if there is a failure in the conduction of this signal to the patient's ventricle, a stimulating signal will in any case be applied to the patient's ventricle 42. It is desired to utilize the rate of the beating atria to synchronize the ventricular pacing which may be impaired because of a myocardial infarction or otherwise defective cardiac conduction system. As shown in FIG. 4C, the cycle begins at time $t_0$ with the sensing of the atrial P wave. As shown in FIG. 4C, a single cycle is divided into six timing periods (and states). During the first timing period from $t_0$ to $t_1$ (as well as the second and third timing periods to time $t_4$) the atrial amplifier 141 is clamped to ground by a timing signal applied to close the switch 130d. Also in the initial period the unclamped ventricular sense amplifier 139 applies any R wave signal applied from the ventricle 42 via the lead 19 to a switch 106a', which is closed by an RV control signal. If during the initial period from $t_0$ to $t_1$, an R wave signal is sensed, the timing cycle is reset to $t_0$. In the second or pulsing period from $t_1$ to $t_2$, the atrial amplifier 141 remains clamped to ground, the switch 130d being closed, and a timing control pulse $T_{WV}$ is applied via the driver amplifier 134a and the resistor $R_{V2}$ to the base of the ventricular output transistor $Q_V$, whereby the previously charged ventricular output capacitor $C_V$ discharges through transistor $Q_V$ via the lead 19 to the patient's ventricle 42. Also during the second period (also extending into periods three and four to time $t_4$), the ventricular amplifier 139 is clamped to ground by a switch 130c to which is applied a clamp ventricular signal TC1, whereby heart activity as would appear in the post-ventricular stimulating period is ignored. In the fourth and fifth periods from $t_3$ to $t_5$, the atrial amplifier 141 is unclamped permitting the atrial P wave signal to be applied thereby via a closed select switch 106b' to reset the timing process to $t_0$. From $t_3$ to $t_5$, a sense timing signal RA is applied to close the switch 106b'. In normal operation, it is contemplated that an atrial P wave signal may be sensed during the fourth and fifth timing periods from $t_3$ to $t_5$, whereby the timing cycle is reset to zero. If however no P wave is sensed, the ventricle is again stimulated by the application of a control pulse $T_{WV}$ to the base of the ventricular output transistor $Q_V$ whereby a pulse is applied via the lead 19 to the patient's ventricle 42, as explained above.

The ASVIP method of pacing may be programmed illustratively in a manner similar to that shown with respect to FIG. 5 with six periods or output states defined in a similar manner and with each of the six timing periods established by addressing or establishing pointers to corresponding tables, whereby varying values of the periods are sent into a timing counter to be decremented as the process is executed through each of six loops.

Figure 6:
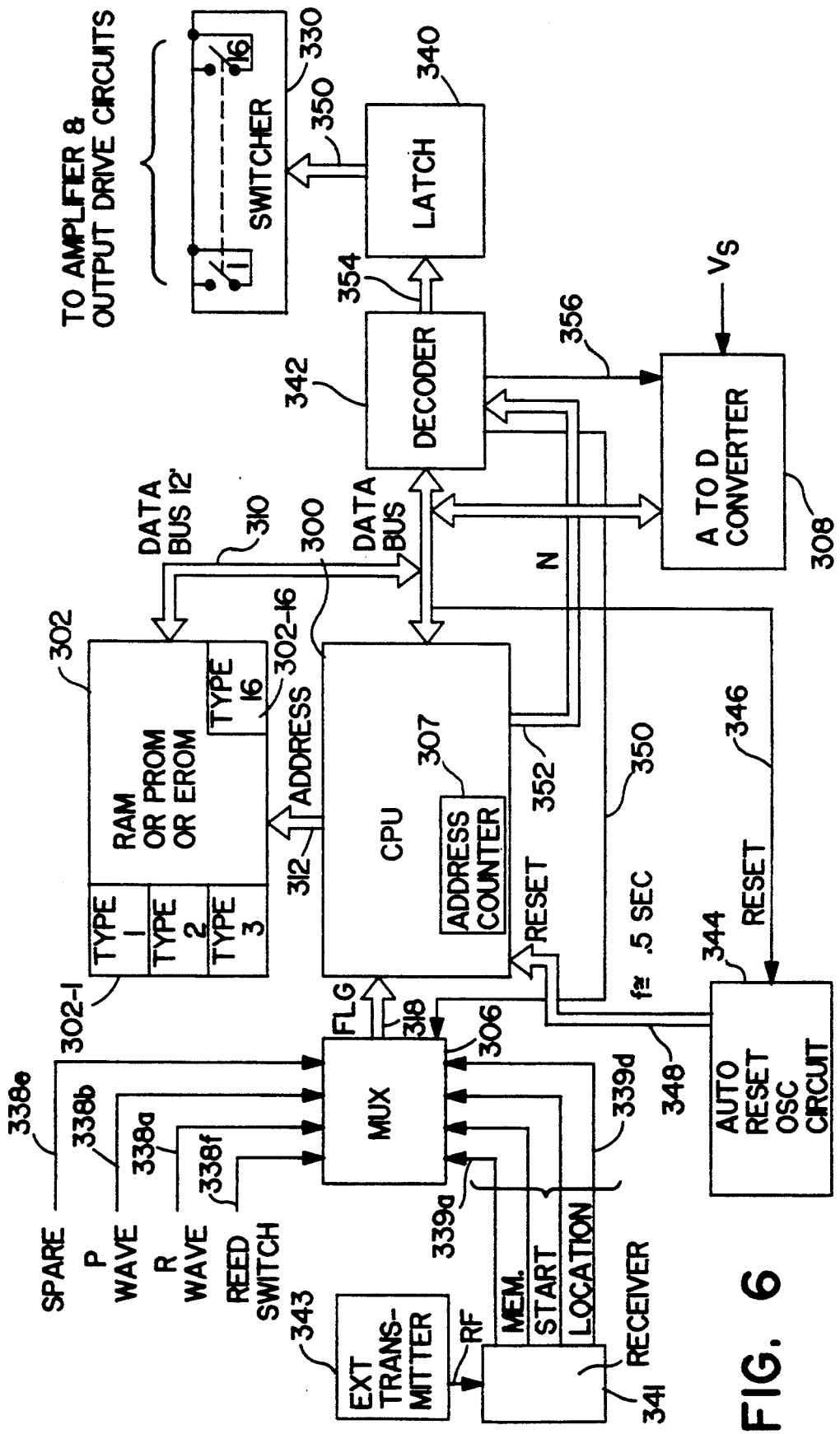
FIG. 6 is a functional block diagram of a further embodiment of the pacemaker of this invention.

Referring now to FIG. 6, there is shown an alternative embodiment of the adaptable programmable pacemaker of this invention, wherein similar elements and circuits are identified with similar numbers to that shown in FIG. 2, except being numbered in the 300 series. For example, the microprocessor or CPU is identified by numeral 300 and is coupled to a multiplexer 306, whereby a selected one of the inputs 338a, b, e or f is applied in the form of a flag via bus 318 to the microprocessor 300. The microprocessor selectively addresses via address bus 312 a memory 302 having illustratively a plurality of sections 302-1 to 302-16. As shown in FIG. 6, the memory 302 may take the form of a volatile memory such as a random access memory, or a programmable read only memory (PROM) or an erasable read only memory (EROM). The addressed data is read out from the memory 302 and applied to a data bus 310 interconnecting the memory 302, the microprocessor 300, a decoder 342 and an A/D converter 308. The A/D converter 308 converts the analog value of the supply voltage $V_s$ to a digital form to be input to the microprocessor 300 via data bus 310. It is understood that the other analog values, such as the P and R waves are also converted to digital form and scaled before application to the multiplexer 306; the A/D converter and the scaler circuit, as would be coupled to the multiplexer 306, are similar to that described above and are not shown in FIG. 6. The microprocessor 300 applies timing signals via an N bus 352 to command the decoder 342 to initiate decoding of the signals appearing upon the data bus 310. The decoder 342 interprets the output of the microprocessor 300 to select one of a plurality of switches 1 to 16 within the block 330. In this regard each such switch of the block 330 has its own latch within block 340 that is set by the output of the decoder 342 and in turn is coupled to an amplifier and output drive circuit as described above. In this manner, flexibility is assured to provide a plurality of output circuits which may be coupled by leads to various portions of the patient's heart, as well as to assure the ability to recharge the output drive circuits and to be able to access data at various points either on the patient's heart or on other parts of the patient's body. Thus a telemetry system is provided for transmitting data from or to the programmable pacemaker as shown in FIG. 6.

In a further feature of the embodiment of FIG. 6, an auto-reset oscillating circuit 344 is provided to reset an address counter 307 within the microprocessor 300. The address counter 307 is incremented for each step processed to address the next word location within the memory 302. It has been found that noise such as generated by a defibrilation pulse or other source, could effect the address counter 307 to address a meaningless or erroneous location within the memory 302. As a result the process would become "hung up" in a meaningless location. If the address would be effected by noise to address a meaningless location, the autoreset oscillator circuit 344 resets on a regular basis, e.g., 0.5 seconds, the address to an initial starting address of the program being executed. In the event that the address counter 307 is operating normally, an output is derived from the data bus 310 and is applied via the conduit 346 to reset the circuit 344, thus inhibiting its regular reset output signal.

In a further feature of this invention, the multiplexer 306, includes an additional set of inputs 339a to 339d for receiving a binary, starting address to be placed into the address counter 307, whereby each of the plurality of blocks 302-1 to 302-16 may be selected and executed. Thus, it is contemplated that a plurality of heart pacing modes could be stored within the memory 302, with each mode stored in a separate block and its starting point could be addressed by entering a binary number via the inputs 339a to 339d and an external link 341 taking the form of an RF (or acoustical) link, as described above.

In addition, self-checking routines or data gathering routines may be stored within designated of the blocks of the memory 302. In FIG. 3A, there is shown an indication of the manner in which an exemplary self-checking routine could be carried out to test the continuing operability of the ventricular sensing amplifier 139. A further select switch 130g may be closed in response to a test signal $T_t$ that is generated by such a self-checking routine or program as stored within the memory 102, to apply a reference voltage $V_{ref}$ in the order of 1 millivolt to the input of the ventricular sensing amplifier 139. The amplified output is in turn applied by the multiplexer 106 to the microprocessor 300; whereby the amplified voltage is compared with a reference value to determine whether the amplifier 139 is operative; if not, a different output circuit and sensing amplifier could be coupled in circuit to replace the defective sensing amplifier.

In a still further mode of operation, a program could be stored within one of the blocks of the memory 302 to effect a sensing and transmission of data as coupled by leads to the implanted pacemaker. For example, the leads could be coupled to heart tissue, other tissue or transducers, to sense the patient's EKG, pulse rate, pulse width, the time of depolarization between the atrium and ventricle, etc. The time of transmission of a depolarization signal is considered to be indicative of the heart's condition and a window is established by a sensing program in accordance with a normal transmission time. If the received signal is outside the limits of such a window, an indication thereof is transmitted externally of the pacemaker. In a data gathering mode, it is contemplated that the latches associated with the associated leads to the heart sites, tissue sites, or transducers are coupled one at a time, by selectively closing the corresponding select switch 330, whereby that data is sent by the receiver 341 to an external monitoring device.

In addition, there is included an input 338f coupled to the reed switch 23 of the type that is closed by an external magnet, to alter the operation of the pacemaker shown in FIG. 6. It is contemplated that a succession of signals may be generated by opening and closing the switch 23, whereby the receiver 341 is enabled to receive or to transmit data to or from the pacemaker 12'; for example, the address counter 307 is loaded with a new address to address the starting location of the next block of memory 302, whereby a further mode of operation is executed.

Figure 7A:
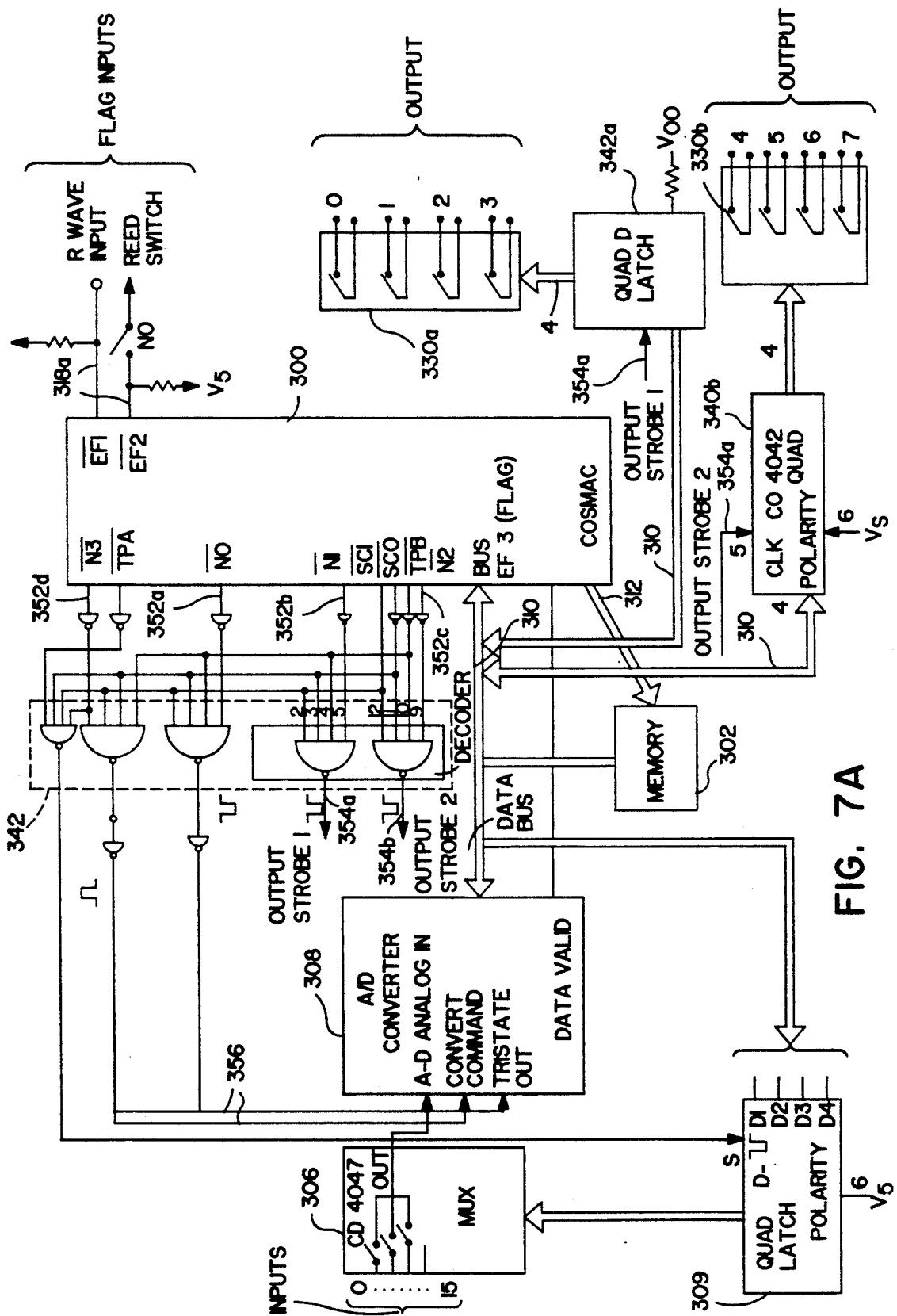
FIGS. 7A and B are detailed circuit diagrams of two specific, illustrative embodiments of the pacemaker shown generally in FIG. 6.

Referring now to FIG. 7A, there is shown a more detailed schematic circuit of the blocks of a first specific embodiment of the apparatus generally shown in FIG. 6. In particular, the microprocessor 300 is identified illustratively as the COSMAC microprocessor as manufactured by the Radio Corporation of America and described in the publication entitled "USER MANUAL FOR THE CDP 1802 COSMAC MICROPROCESSOR (1976)". The multiplexer 306 has a series of sixteen inputs 0 to 15 and may take the form of the CD0067 as manufactured by RCA to provide an output to the A/D converter 308, an illustrative embodiment of which will be described later with respect to FIGS. 8, 9 and 10. In turn, the A/D converter 308 is coupled by the data bus 310 to the microprocessor 300, and is also connected to a latch 309, whereby one of the sixteen inputs of the multiplexer 306 is selected to apply analog data to the A/D converter 308. The N timing bus 352 is shown as a bundle of conduits 352a to d and is coupled to the decoder 342 made up of a plurality of gates as manufactured by RCA under a designation CD4012. The outputs of two of the gates are applied via the conduits 356 to a convert command input, whereby the A/D converter 308 accepts data from the multiplexer 306, and to a tristate output, whereby the A/D converter 308 is commanded to apply the data converted to digital form to the data buss 310. Further, output strobes 1 and 2 are derived from conduits 354a and b, and applied respectively to latches 342a and 342b, whereby data applied to the data conduit 310 may be selectively applied to one of a plurality of switches contained within the blocks 330a and 330b, respectively. The blocks 330a and 330b each include four solid state select switches to provide output signals to selected output drive circuits. Further, in the particular embodiment shown in FIG. 7A, the detected R wave signal is applied to the $\overline{EF1}$ input of the microprocessor 300, and the reed switch input is applied to the $\overline{EF2}$ input of the microprocessor 300. In this embodiment, the microprocessor 300 acts as its own multiplexer to selectively access and operate upon signals placed to these inputs in the desired sequence. Further, the microprocessor 300 applies addresses via the address bus 312 to the memory 302 whereby data may be read out and applied to the data bus 310.

Figure 7B:
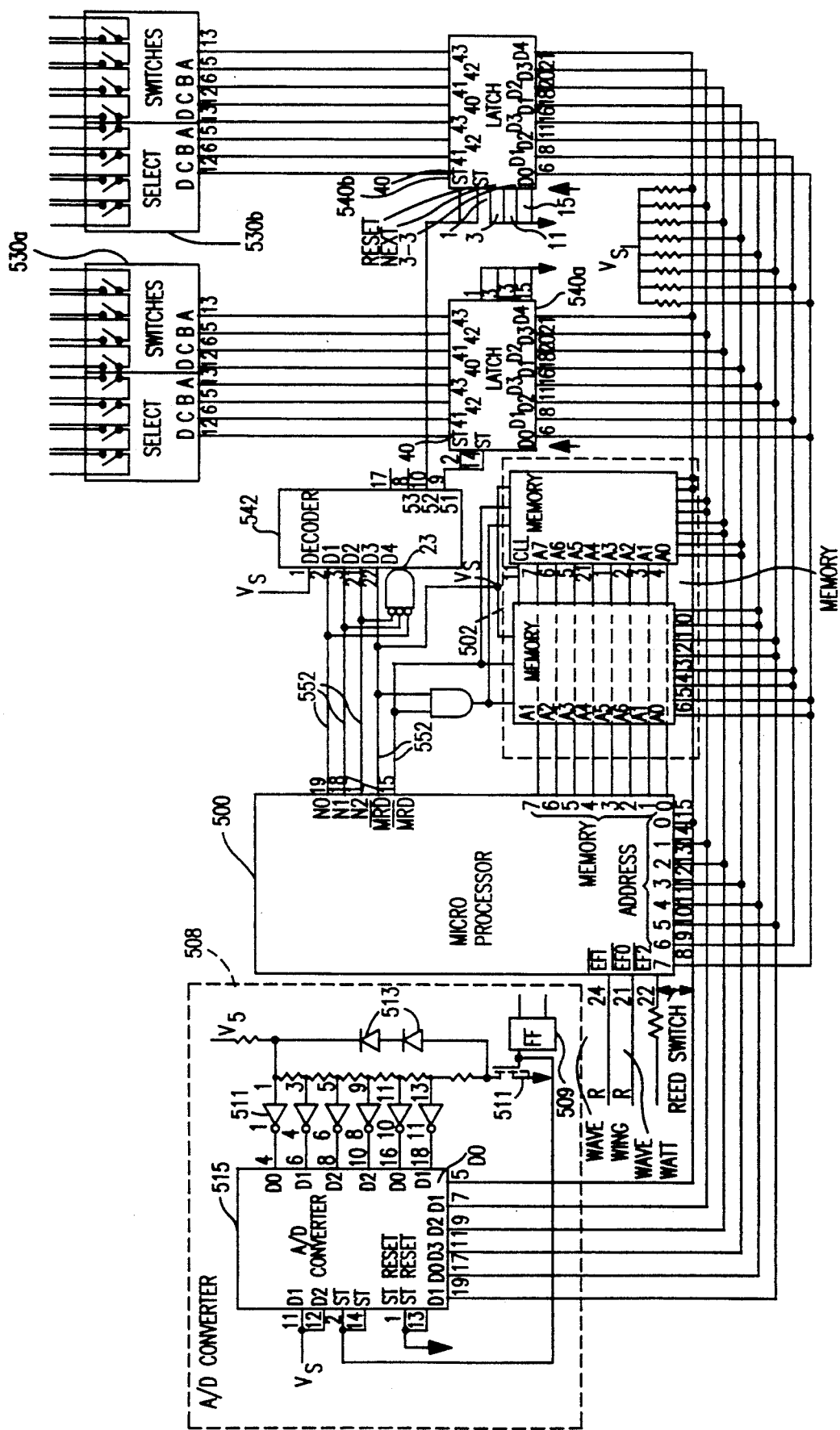

In FIG. 7B, there is shown a detailed schematic circuit of a further second embodiment of the pacemaker apparatus as shown generally in FIG. 6. The elements in FIG. 7B are numbered with the same number as like elements of FIG. 6, except in the 500 series. The input signals corresponding to the R wave, the P wave and the reed switch output are applied to the inputs $\overline{EF1}$, $\overline{EF0}$ and $\overline{EF2}$ of the microprocessor 500, which may illustratively also take the form of the CDP 1802 microprocessor manufactured by RCA. In this embodiment, the microprocessor 500 performs multiplexing functions whereby one of these values is processed at a time. Typically such inputs are in analog form and require conversion to digital form by the circuits shown within the dotted lines marked generally by the numeral 508. The A/D converter includes a circuit as manufactured by RCA under their designation CD4506 and receives inputs from operational amplifiers 511 to which is applied a reference signal established by the Zener aiodes 513. A clock signal is applied via a flip-flop 509 and an FET 517 to an input of the converter 515. The system's memory 502 is connected to outputs of the microprocessor 500 and is comprised of two blocks manufactured by RCA under their designation CDP 1822S. The microprocessor 500 supplies command signals via the N bus 552 to a decoder 542 taking the form of a chip as manufactured by RCA under their designation CD 4514B. The decoder 542 performs decoding functions on the output of the memory 502, under control of the timing signals applied via the N bus 552. The outputs of the decoder 542 are applied to a pair of latches 540a and 540b, each taking the form of the latch as manufactured by RCA under their designation CD4508. The decoder 542 selects a latch whereby a corresponding select switch within the arrays 530a and 530b is closed. The arrays of select switches may be composed of integrated circuits as manufactured by RCA under their designation 4066AE.

Referring now to FIG. 8, there is shown an illustrative embodiment of a low power A/D converter 308 as incorporated into the pacemaker as shown in FIG. 7. As shown in FIG. 8, an analog voltage V(x) to be converted to digital form, is applied by input line 404 to a switch (S$_1$) 407 which is connected to an up or first position to apply the analog voltage V(x) to the input (V$_{IN}$) of a voltage control oscillator (VCO) 402, whose output is applied to the input of an accumulator counter 400. As indicated by the inputs to the counter 400, the accumulator counter 400 is capable of counting either "up" or "down" to provide an output via gate 414 to an input of an "M" output counter 412. A clock signal is applied via an input line 418 to control logic 408 and in particular to divide by N circuit 410, whose output is coupled to throw switch 407 to a second, down position, whereby a reference voltage is applied via conductor 406 to the input of the VCO 402, and at the same time a down command signal is applied via gate 418 to the down input of the accumulator counter 400, which then initiates a counting down mode. At the same time an output from the control logic 408 is applied to the reset of the "N" output counter 412.

The A/D converter 308 of FIG. 8 operates in the following fashion. An unknown voltage $V_x$ is applied to the VCO 402 via switch 407 for a fixed period of time $T_{up}$. During this time period $T_{up}$, accumulator counter 400 is counting up the output of the VCO 402. The accumulator counter 412 is acting very much like an analog integrator in that the count of the accumulator counter 400 is building up at a linear rate for a given voltage level of $V_x$.

Time $T_{up}$ is dependent upon the clock frequency applied to line 418 through the control logic 408 and the "N" counter 410. At the end of time $T_{up}$, switch S1 is disposed to its second position to connect the input of the VCO 402 to the reference voltage $E_{ref}$. Coincident with this switching to the reference voltage, the "A" accumulator counter 400 is placed in the down count mode. During this down count, circuitry is employed which examines when accumulator counter 400 has counted back to a predetermined count, e.g., zero. The time required to count the reference voltage back to zero is proportional to the average value of the input voltage, $V_x$. While the accumulator counter 400 is being counted back to zero the clock frequency, $F_{CLK}$ is counted by the "N" output counter 412. Counts accumulated in the "N" counter 412 are in digital form and are directly proportional to the initial unknown voltage, $V_x$. This results in a voltage to frequency conversion.

The basic equations for the operation of the A/D converter 308 are:

$$A_{up} = K_{VCO}\overline{V(x)}\, T_{up} \qquad (1)$$

$$A_{DWN} = K_{VCO} E_{ref} T_X \qquad (2)$$

Equations 1 and 2 give the up and the down count of accumulator counter 400 as a function of the unknown voltage and the reference voltage, and the length of time this voltage is applied to the VCO 402. The up count and the down count of the counter 400 are equal since the counter 400 is starting from zero and returning back to zero at the end of a cycle. Equating these two equations results in the elimination of the voltage controlled oscillator scale factor $K_{VCO}$ from the effect on output of the A/D conversion. Equation 3, which gives the output counter accumulated count N(X) as a function of the clock frequency $F_{CLK}$ and the length of time required to force the accumulator counter back to zero, that is, $T_X$, is reproduced as follows:

$$N(X) = T_X F_{CLK} \qquad (3)$$

Equation 4, which gives the up count time, $T_{up}$, as a function of the "n" counter and the clock frequency, is as follows:

$$T_{up} = n/F_{CLK} \qquad (4)$$

Equation 5, which shows that the output counter count N is proportional to n and the unknown voltage divided by the reference voltage, is as follows:

$$N(x) = n\frac{\overline{V(x)}}{E_{ref}} \qquad (5)$$

Equation 5 shows that the digital output count N(x) is independent of the clock frequency $F_{CLK}$, the strobe frequency, and of particular interest, the VCO scale factor. For example, if the unknown voltage, $V_X$ were two volts, the reference voltage were two volts and the n counter output was 64; at the end of each conversion output counter N would have a count of 64 in it. This particular characteristic of the A/D converter allows us to put a gain in series with switch S1 and the VCO 402 and essentially not effect the output count even if this gain were to change or be different from unit to unit provided that the gain were constant over one conversion cycle. In other words, as shown in FIG. 8, since a single VCO 402 is used to apply both the input analog voltage V(x) as well as the reference voltage $E_{REF}$, the scaling factor as imposed by the VCO 407 does not effect the digital output of the counter 412. Further since the same clock signal $f_{CLK}$ is used to clock the first or accumulator counter 400 during the down period $T_X$, as well as to clock the "N" output counter 412 for the same period, the frequency of the clock signal $f_{CLK}$ does not effect the digital output of the counter 412 indicative of the amplitude of the input analog signal V(x). Thus, the clock used to supply the clock signal $f_{CLK}$ does not have to be of the high precision, relatively high power drain variety, but may be configured to impose a minimal drain upon the power source, i.e., the pacer's battery.

Figure 10:
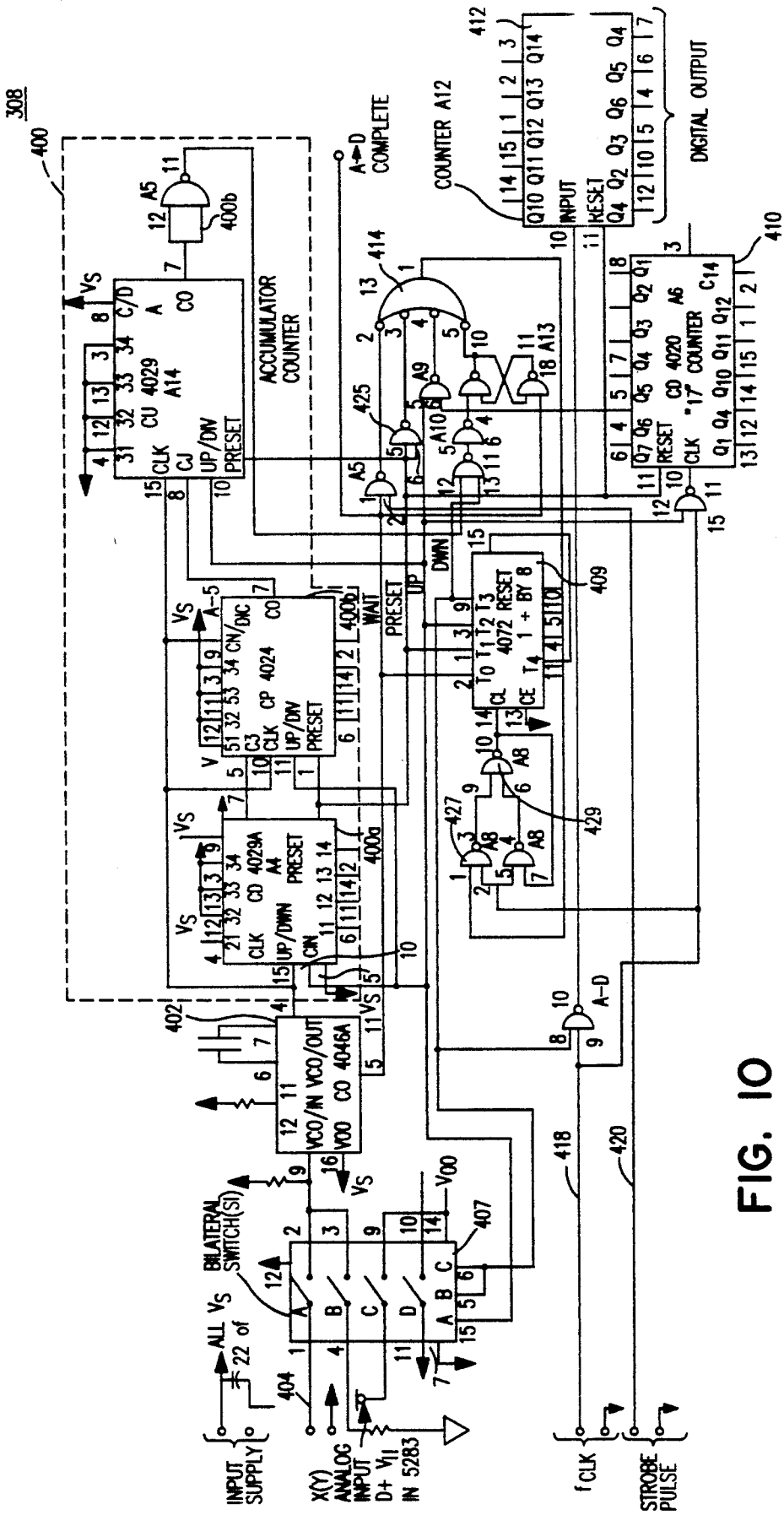
FIG. 10 is a more detailed circuit diagram of the A/D converter shown in FIG. 8.

In FIG. 10, there is shown a detailed circuit implementation of the A/D converter 308 generally shown in FIG. 8. The input is applied to a bilateral switch taking the form of the switch 407 whose output is in turn applied to the VCO 402 contained in a phase lock loop circuit. In turn, the VCO output is applied to the accumulator counter 400 comprised of four up/down counters CD4029A. The clock frequency $F_{CLK}$ is applied with the strobe pulse via conductors 418 and 420 respectively to time the output of the accumulator 400 to the N output counter 412. A key part of the illustrative implementation of the A/D converter 308 is to design the control circuit 408, as shown in FIG. 8, to include a counter 409 in the form of a four-bit ring counter. This counter 409 forces the A/D converter 308 into one and only one of four possible modes, corresponding to its four output states 0, 1, 2 and 3. These four modes of operation of the A/D converter 308 as shown in FIG. 10, are: (1) wait; (2) preset; (3) up count; and (4) down count.

The wait mode is a resting mode for the A/D converter 308 in which the VCO 402 is turned off, the unknown and reference voltages are disconnected via bilateral switch 407 from the VCO 402, and the last converted digital word is resting in counter 412 as a digital, parallel eight bit word. The converter 308 rests in this wait mode until it receives a strobe pulse which drives it to the preset mode. Very low power is drawn by the A/D converter 308 while in the wait mode.

The preset mode follows the wait mode and is used for presetting the accumulator comprised of counters 400a, 400b, and 400c, to a binary word of one via a jam input. Counter 412 is reset during the preset mode. The maximum time the preset mode exists is one-half of a clock period.

During the up mode, output 3 of the divider 409 is energized to logic 1 which forces accumulator counters 400a, 400b and 400c to count in the up mode. During this mode bilateral switch S1 directs the unknown analog input to the input of the VCO 402. Also "N" counter 410 begins to time the length of time the unknown voltage is applied by counting the reference clock frequency to the preprogrammed count which will bring the output of AND gate 425 to a logic one. During this mode, counts are accumulated in the counters 400a, 400b and 400c. When the output of AND gate 425 reaches a logic one indicating the up count time period has been reached, it inputs are both logic one and a command to advance the ring counter 409 is applied to the pulse stretcher gate 427. At the next clock pulse reaching logic one drives ring counter 409 to the next state which is the down count.

A down count mode is established by energization of the output 7 of the ring counter 409 to a logic one. This condition forces the accumulator counter 400 to count down. Also the reference voltage is applied to the voltage controlled oscillator 402. Also the clock frequency is directed to the input of N counter 412. Thus as the counts are driven out of accumulator counters 400a, 400b, and 400c, clock pulses are being accumulated in N counter 412. When the accumulator counter chain has driven to logic zero in all states, the output of AND gate 429 rises to logic one and forces the ring counter 409 to its wait mode through the pulse catching network described previously. The completion of this cycle results in unknown input voltage V(x) being digitized and held in output counter 412 with the scale factor as described above.

The A/D converter 308 as shown in FIGS. 8 and 10 is particularly designed to be incorporated within the pacer 12, as shown in FIG. 1. As indicated above, it is significant to incorporate within the pacer, circuitry that will impose a minimum drain upon the pacer's power source, e.g., its battery. To this end, the circuitry as illustratively shown in FIG. 10 may be implemented by CMOS technology. Secondly, as described above, the oscillator 402 is only energized to provide an output during those times in which an input analog signal V(x) is to be digitized; at other times, the VCO 402 is deenergized. The energization of the VCO 402 is under the control of the control circuit 408 and in particular of the ring counter 409. Thirdly, the A/D converter 308 may be adjusted by incorporating different values of "n" within the counter 410, whereby the A/D converter 308 is adapted to sense input voltages of varying amplitudes. In the various embodiments of the pacer of this invention as described above, it is contemplated that it would be desired to convert the relatively large voltage $V_S$ of the battery, as well as the relatively small voltage signals as derived from the patient's ventricle and atrium. As shown in FIG. 10, the preselected up time period $T_{up}$ is determined by the value of "n" as set in the "n" counter 410. The value of "n" may in one illustrative embodiment of this invention be set by connecting one of the plurality of outputs Q4, Q5, Q6, and Q7 of the N counter 410. It is contemplated that a switch circuit (not shown) could be incorporated between one of the outputs of the counter 410 and the AND gate A9, whereby the value of "n" could be placed under the control of the microprocessor 300, as shown in FIG. 7A. In addition, a programmable counter, as are well known in the art, could be substituted for the present counter 410 whereby a suitable binary word could be stored therein to be varied under the control of the microprocessor. Thus, the value of "n" could be varied dependent upon which input analog signal was to be converted into digital form. The value "n" is varied dependent upon the amplitude of the contemplated input voltage V(x), with larger values of "n" being selected for smaller amplitudes. As a practical matter, it is desired to achieve a count within the output counter 412 close to its known capacity, whereby the maximum resolution for an input signal of given amplitude is assured. Thus, a single analog digital converter 308 may be used for different input signals of varying amplitude, ensuring the precision of the binary output signal by varying the value of "n".

Figure 11A:
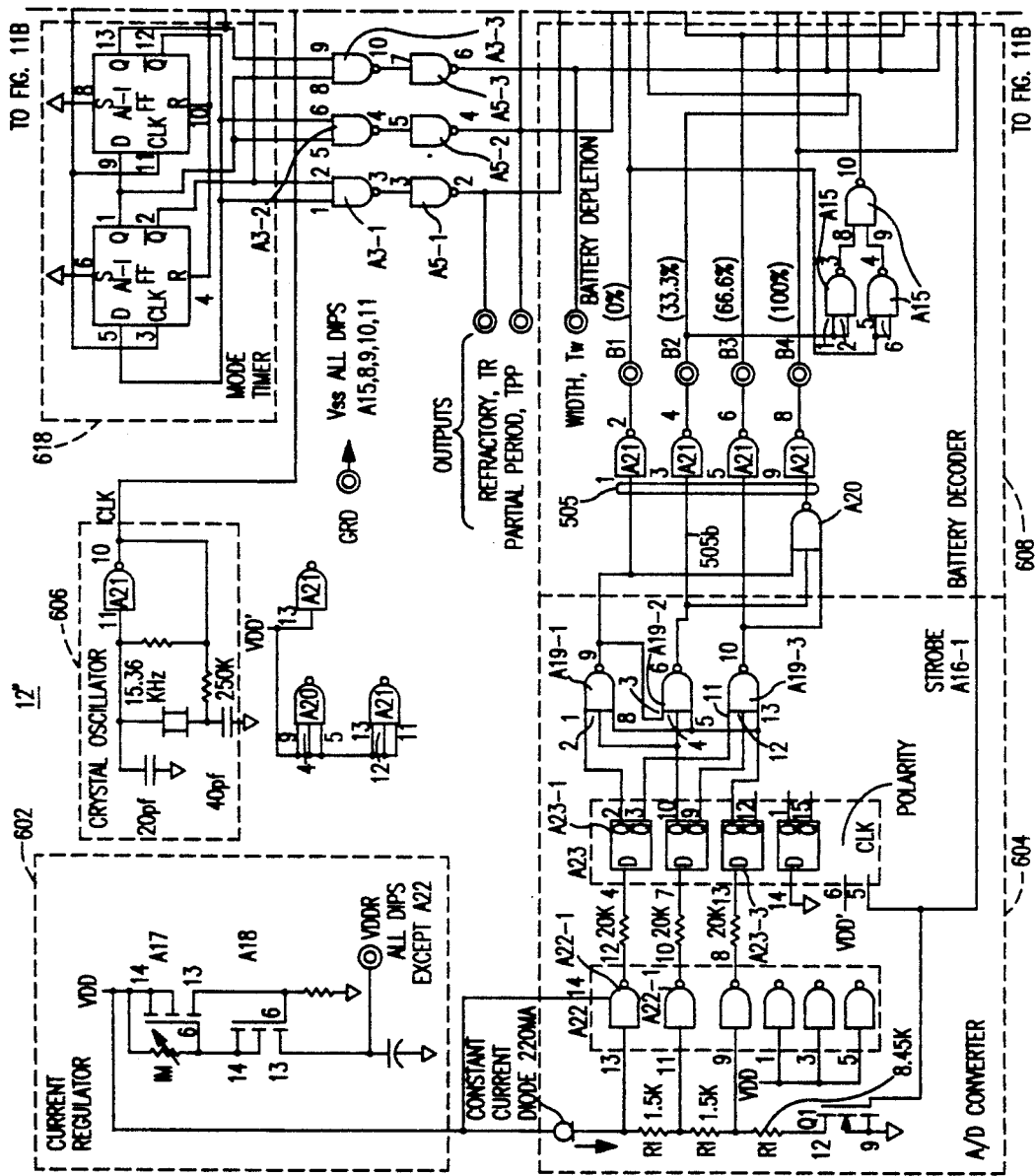
FIGS. 11A and B show a detailed circuit embodiment of a hardwired or permanently coupled digital components implementing the subject invention in a manner similar to that of the microprocessor implemented invention as shown in FIG. 2 as would be programmed with a program of the flow diagram of FIG. 5.
Figure 11B:
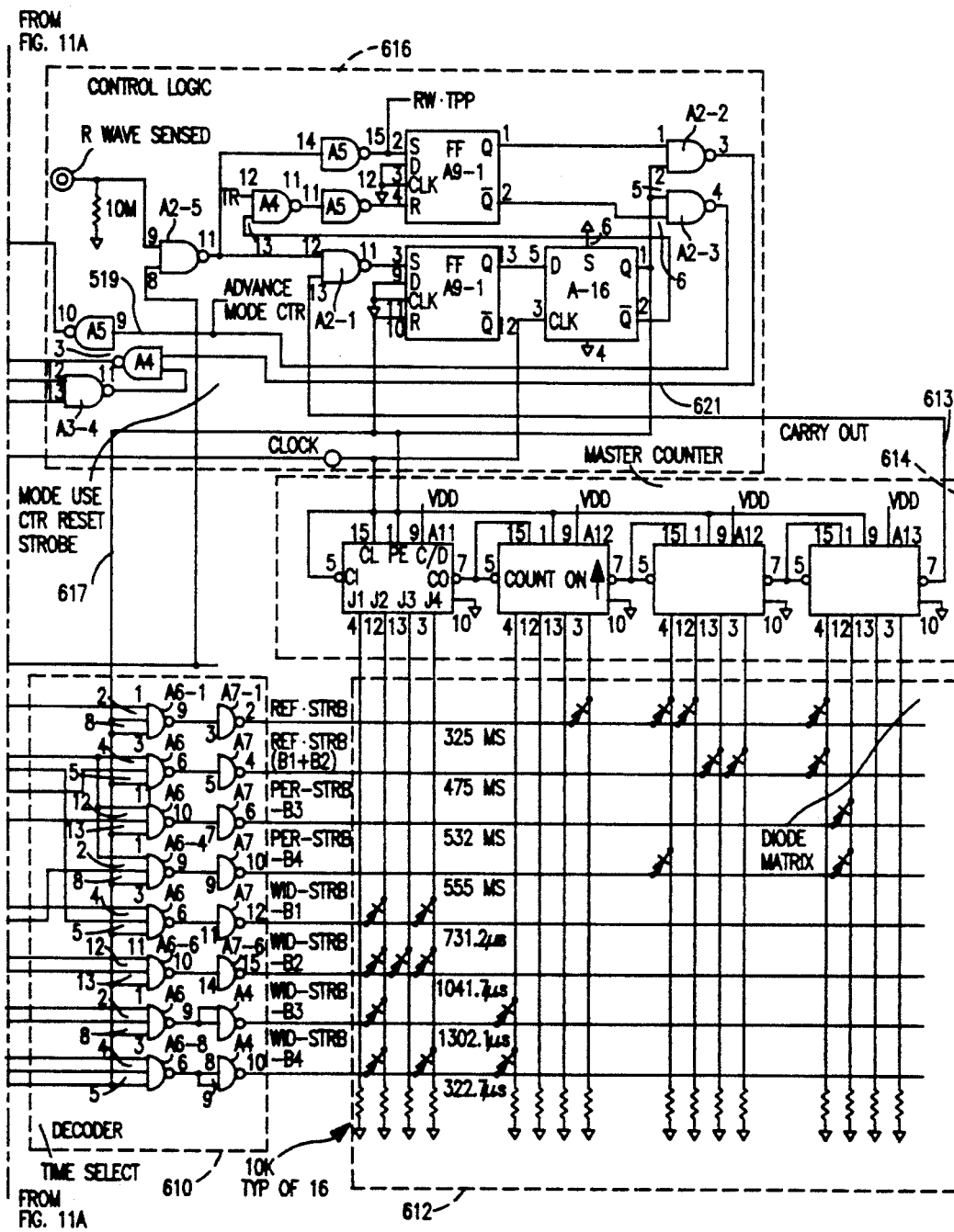

In FIGS. 11A and B, there is shown an embodiment of this invention that employs illustratively off-the-shelf CMOS components that are coupled together permanently, i.e., hardwired, to effect a demand mode of pacing in a manner similar to that described with respect to FIG. 4A wherein the partial and the pulse width periods are adjusted in step fashion as a function of the supply voltage $V_{DD}$. A pacemaker 12" is shown in FIG. 11A as including a current regulator 602 for sensing the level of the supply voltage $V_{DD}$ that provides energization to the elements of the pacemaker 12", for providing a regulated current to an analog to digital (A/D) converter 604 whose four outputs are exclusively indicative of the voltage level $V_{DD}$ of the pacemaker's battery. The mutually exclusive four outputs are applied to a battery decoder 608 to provide mutually exclusive outputs indicative of the battery's output level and therefore its percentage of depletion. The outputs of the battery decoder 508 are applied along with the outputs of a mode counter or timer 618 indicative of which of the three states the pacemaker 12" is in, i.e., refractory period, sensing or partial period, or pulse width, to a time select decoder 610 (see FIG. 11B) which provides a mutually exclusive output upon one of its eight outputs indicative of the desired period to be set into a counter means in the form of a master counter 614. The battery decoder 508 and the time select decoder 510 form means responsive to the state in which the pacemaker 600 is operative and the level of battery depletion for selecting a count to be counted by the master counter 614. As shown in FIG. 11B, the output of the time select decoder 610 is applied to a memory means in the form of a diode matrix 612 which in response to a selected input applies a count corresponding to the desired length of the period to be counted down by the master counter. As will be explained, the stimulating pulse width and the sense or partial period are programmable by the diode matrix 512. Upon reaching zero, the master counter 614 provides an output via a control logic circuit 616 to the mode timer 618 to advance the mode timer 618 to its next state to thereby provide an output to set the pacemaker 600 in its next timing operation. The control logic 616 also includes resetting means responsive to the input of an R-wave provided by an R-wave sensing amplifier associated with a lead coupled to the patient's ventricle to thereby reset the mode timer 618 to its initial or refractory period. In addition, the control logic 516 also controls the loading of the data indicative of the mode and battery depletion level from the decoder 610 to the matrix decoder 612.

The pacemaker 12" is configured to operate in a demand mode and includes the mode timer 618 in the form of a three-state counter to keep track of the sub-intervals or periods corresponding to the refractory period, the partial or sense period, and the stimulating pulse width as shown in FIG. 4A. The mode timer 618 is comprised of a pair of flip-flops A1 and has three output lines which are mutually exclusive and determines a unique sub-interval or period of the pacemaker's cycle. Though illustratively three sub-intervals were selected, theoretically the oscillator cycle could be broken into many sub-intervals. For example, if a pulse was required during refractory period to charge the output capacitor, the mode timer 618 could easily be adapted to break the refractory period into two further sub-intervals.

As will be explained, the pacemaker 12" of FIGS. 11A and B is similar in operation to the microprocessor controlled pacemaker 12 of FIG. 2 as programmed with the process as illustrated by the flow diagram of FIG. 5. In particular, each of the noted sub-intervals are timed by presetting a number or count into a single counter, i.e., the master counter 514, which is a 16-bit binary counter and which counts the inputted number to zero in response to the clock output of the crystal oscillator or clock 606. Illustratively, the output of the crystal oscillator 606 is a 15.36 Khz clock signal. The master counter 614 is illustratively comprised of 4-bit binary counters A11, A12, A14, and A13, which are configured in a ripple configuration in order to reduce the overall current drain by a reduction of loads as imposed upon the clock line, i.e., the output of the crystal oscillator 606. In the embodiment shown in FIGS. 11A and B, three separate counts are strobed into a single master counter 514; a first clock cycle is used to strobe the program count from the diode matrix into the 16-bit binary master counter 514 at the beginning of the timing cycle, and one clock pulse is used at the end of the timing cycle to advance the mode timer 618 to the next sub-interval. Within the present illustrative system, virtually any program time is possible for any of the aforementioned sub-intervals within the range of three clock periods to 65.5 Khz clock cycles. With a 15.36 Khz clock signal, this is equivalent to a timing range of 1975 microseconds to 4.2 seconds.

The bookkeeping and sequencer logic or control logic 516 comprises flip-flops A9 and A16, and associated gating circuitry to provide an output signal at the beginning of the timing cycle to load the appropriate word or count into the master counter 614 to provide an output signal to advance the mode counter or timer 518 at the end of the timing cycle and to permit the R-wave interrupt to occur only during the partial or sense period. The diode matrix 612 is utilized to load the appropriate binary word or count into the master counter 614. A single line of the diode matrix 612 is addressed by the time select decoder 510. Diodes are selectively connected from the input or horizontal lines to the output or vertical lines which in turn are connected to the jam inputs of the master counter 614 whereby a change of count merely involves the shifting of the position of the diode. It is contemplated that if the invention were implemented by a large scale integrated chip, a programmable logic array, such as a mask programmable read-only memory (ROM), a programmable read-only memory loaded at the time of manufacture, an EROM or PLA's would be used.

The pacemaker 600 includes means for stretching the pulse widths and sensing periods as the output level of the supply voltage or energy source decreases. The stretching means includes the A/D converter 604 comprised of flip-flops A22, A23, and A19. The output of the A/D converter 504 comprises four lines mutually exclusive which are used to steer the appropriate address line in the diode matrix 512 via the battery decoder 608 and the time select decoder 610. In particular, the time select decoder 510 has eight outputs, one to set the period of the refractory period, three to set the count corresponding to the length of the partial or sense period, and four to set the width of the stimulating pulse.

In particular, the output $V_{DD}$ of the voltage supply or battery, which energizes the current regulator 602 to provide a regulated current to the A/D converter 504 which provides constant but different voltages at the inputs of a plurality of inverters A-22 as taken from the points of interconnection of resistors R1, even as the supply voltage $V_{DD}$ decreases with use. As the supply voltage $V_{DD}$ drops, the logic state as appears at the output of the inverter switches A22 switches from a logic "1" to a logic "0". Thus utilizing three inverters A22, a range of changes of the supply voltage may be indicated. In order to reduce the current drawn by the A/D converter 604, a switch Q1, in the form of an FET, is strobed for one clock period and the voltage levels, as appear at the points of interconnection between the resistors R1, are applied via the inverters A22 into a corresponding set of latches A23.

In the embodiment shown in FIG. 11A, the strobe signal is derived from the Q output of the flip-flop A16 and occurs once for each of the three periods, i.e., refractory, sense, and pulse width periods, to thereby turn on the FET Q1 at each instance thereof. In a preferred embodiment of this invention, the FET Q1 is replaced by a further D-type flip-flop, whose D input is strobed by a signal derived from the output of the NAND gate A7-1 (see FIG. 11B) corresponding to the occurrence of the refractory period and the strobe signal. Thus, upon the occurrence of the next clock signal as applied to the CLK input of this D-type flip-flop, an output will be derived from the D-type flip-flop and applied to the series connected resistors R1, whereby the energy level $V_{DD}$ of the energy source, e.g., the pacemaker's battery, is sampled and applied to the NAND gates A22 for a period corresponding to the width of one clock pulse. In this manner, a drain is placed upon the pacemaker's battery only once in the cycle of operation of the demand pacemaker, thereby limiting the current drain upon the pacemaker's battery.

The operation of the pacemaker 600 of FIGS. 11A and B, will now be explained in greater detail with respect to FIGS. 4A and the steps of the flow diagram of FIG. 5. Initially, as shown in steps 208 through 220, and A/D conversion is effected whereby a count dependent upon the level of the supply voltage $V_{DD}$ is loaded into a single master counter 614. First, as in step 208, the A/D converter 604 provides upon one of its four outputs 605, an output indicative of the degree of depletion of the voltage supply $V_{DD}$. In particular, a regulated current is applied to a constant current diode to establish voltages at the points of intersection between the resistors R1. In a preferred embodiment of this invention, the current regulator 602 and the constant current diode, as shown in FIG. 11A, may be replaced by a zener diode or a pair of series connected zener diodes, which are connected to the voltage $V_{DD}$ and in parallel with the series connected resistors R1 to provide a constant current flowing through the series connected resistors R1. The advantage of such a preferred embodiment is increased stability with changes of temperature. The inverters A22 act as comparing means to effect the step 212 whereby the voltage $V_{DD}(V_p)$ is compared with a series of discrete levels. For example, if the energy source in the form of the pacemaker's battery is operating at its normally high level, i.e., 0 depletion, a voltage of a relatively large magnitude is applied to the inverter A22-1 sufficient to place it in its "1" state, whereby a "1" is applied to the corresponding latch or flip-flop A23-1 to set its Q output to a high state thus supplying a high or "1" signal to a first input of a NAND gate A19-1. The other inputs of the NAND gate A19-1 are derived from the Q outputs of the latches A23-2 and A23-3, which are also high or "1" in that each has been set by corresponding high or "1" signals derived from the inverters A22-2 and A22-3. If the level $V_{DD}$ of the supply voltage falls below a level indicating that a third or 33⅓% of the battery life has been depleted, the voltage level appearing at the input of the inverter A22-1 will be such that a low or "0" output will be applied to the input of the latch 23-1 whereby its Q output will be applied to the input of the latch 23-1 whereby its Q output will be set to zero and the output of the NAND gate A19-1 will be driven to a "1". In this state, the inputs of the NAND gate A19-2, as derived from the outputs of the NAND gate A19-1 and the Q outputs of the latches A23-2 and A23-3 will be all "1" to thereby provide a "0" output from the NAND gate A19-2. In similar fashion, as the voltage level $V_{DD}$ falls, the output of the NAND gate A19-3 will also be disposed to "0". A fourth NAND gate A20 is connected to each of the outputs of the NAND gates A19 to provide a further "0" output in the case all of the NAND gates A19 are disposed in their "1" state. As shown in FIG. 11A, the outputs of the NAND gates A19-1 to A19-3, and the NAND gate A20 are applied to corresponding inverters A21 to thereby provide a mutually exclusive "1" or high output signal therefrom depending upon the voltage level $V_{DD}$; in particular, the "1" signal will appear on that output corresponding to a 0, 33⅓, 66⅔, and 100% battery depletion and will be applied to the time select decoder 610.

As shown in FIG. 11A, the mode timer 618 initially is set, as in step 216, to its refractory state to provide a "1" at its refractory output. In particular, each of the A1 flip-flops are reset by a signal applied to their R inputs from the reset line 621 disposing their Q outputs to a "1" state whereby the inputs to a NAND gate A3-1 are driven high to provide a "0" output to the input of the inverter A5-1, whose output is a high or "1" signal. Thereafter, in step 220, the manifestation of the voltage level $V_{DD}$ as converted to digital form by the A/D converter 604, is applied by the time select decoder 610 to the diode matrix 512 whereby a count in the form of a binary word is applied to the 4-bit binary counters A11, A12, A14, and A13 of the master counter 614. In particular, one of the mutually exclusive outputs of the battery decoder 608 is rendered high or a "1" indicating a corresponding level of battery depletion. The battery decoder output and mode timer output are both applied to the time select decoder 510 which provides a "1" signal upon one of its mutually exclusive outputs to select a count dependent upon both the battery depletion and the state in which the pacemaker 600 is in, i.e., refractory, partial, or pulse width state. The time select decoder 610 comprises a plurality of NAND gates A6 and a corresponding plurality of inverters A7. One input of each of the NAND gates A6 is connected to a strobe line that is coupled to the control logic 616 to time the application of the input to the diode matrix 612. In addition, one of the other inputs of the NAND gate A6 is applied to the mode timer 618 to sense the particular mode and the other input is coupled to one of the four outputs from the battery decoder 608. In the refractory mode, a "1" signal is derived from the inverter A5-1 and upon occurrence of the strobe signal, the NAND gate A6-1 is rendered low whereby its corresponding inverter A7-1 is rendered high to apply a "1" signal to the corresponding input line of the diode matrix 512, and a corresponding binary signal, as defined by the diodes as shown in FIG. 11B, is applied to the inputs of the binary counters comprising the master counter 614. Next, as indicated in steps 222, 224, and 226, the count as entered into the counter 614 is decremented by 1 until the entered count is counted down to zero. As shown in FIG. 11B, the clock output signal derived from the crystal oscillator 606 is applied via a clock input to the master counter 614 whereby the binary counters A11, A12, A14, and A13 are counted down until a signal is derived from the output of the binary counter A13 of the master counter 614 and is applied via the line 613 to the control logic 616 and in particular to its NAND gate A2-1, whereby the flip-flop A9 is set driving high its Q output and the D input of the flip-flop A16. Upon the occurrence of the next clock signal, the Q output of the flip-flop A16 is set high whereby a high or "1" strobe signal is developed upon the output line 617 to be applied to the time select decoder 612 whereby the next manifestation of the battery depletion level is applied to the diode matrix 512. In addition, the high going signal derived from the flip-flop A16 is applied as an advance mode counter signal via the enabled NAND gate A2-3 and the output line 519 to the clock inputs of the flip-flops A1 to advance the state of the mode timer 618. If, as explained above, the mode counter 618 is in its initial or refractory mode, the flip-flop A1-1 is set whereby a high signal appears as its Q output and the flip-flop A1-2 remains with its Q output at a low or "0" state. Thus, in the sense or partial period, high or "1" signals are applied to the inputs of the NAND gate A3-2, whereby a high or "1" signal appears upon the output of the inverter A5-2 indicating that the pacemaker 500 is in its second partial or sense mode.

As shown in FIG. 5, when the master counter 614 has counter to "0" as detected by step 224, the mode timer 618 is advanced to its next or refractory state by step 234. At this time, the mode timer 618 provides a signal indicating that the pacemaker mode is in the sense period and, in step 236, the value of the battery depletion as derived from the battery decoder 608 is applied to the time select decoder 610 to select a particular count from the memory in the form of the diode matrix 612 and to transfer the selected count to the master counter 612. The high or "1" output from the inverter A5-2 is applied to each of the NAND gates A6-2, -3, and -4, whereby depending upon which of the battery depletion outputs is energized, a corresponding NAND gate A6 will be enabled upon the occurrence of the next strobe input appearing on line 617. For example, if the output of the battery decoder 608 indicates that 66.6% battery depletion has occurred, the NAND gate A6-3 will be enabled and a "1" signal is applied via inverter A7-3 will be enabled and a "1" signal is the diode matrix 512, whereby a corresponding count will be entered into the binary counters of the master counter 614. The master counter 614 proceeds to count the inputted count down to "0" to provide an output via line 613 to the control logic 616 to apply, as explained above, an advance mode counter signal via line 619 to the mode timer 618 setting the mode timer 618 to the next state, i.e., the pulse width period.

During the sense or partial period, the control logic is disposed to sense an R-wave as indicated by step 228. If during the sense period the heart provides a naturally occurring heartbeat, it is sensed by the R-wave sensing amplifier and a signal is applied via the R-wave sensed input of the control logic and the enabled NAND gate A2-5 to set the flip-flop A9-1, whereby a "1" signal is developed upon its Q output to be applied via the enabled NAND gate A2-2 and line 621 as a mode counter reset signal to reset the flip-flops A1 of the mode timer 618 to its initial or refractory state.

In the absence of a sensed R-wave, the master counter 614 is permitted to count to "0", as indicated by step 224, whereby the control logic 616 provides a mode advance counter signal, as explained above, to the clock input of flip-flops A1; as a result, the mode timer 618 is advanced to its next pulse width state, as indicated in step 232, to provide an output from the inverter A5-3. In step 236, a count indicative of the length of the pulse width period is entered. In particular, an input as derived from the NAND gate A5-3 is applied to each of the NAND gates A6-5 to A6-8, and dependent upon the level of battery depletion, one of these aforementioned gates is enabled upon the occurrence of the next strobe as derived from the control logic 516, to apply a signal upon the corresponding input line to the diode matrix 612. The diode matrix 512 generates upon its output lines a binary signal indicative of the count to be entered into the binary counters of the master counter 614. The master counter 614 is again counted to "0" to develop a signal upon its output line 613 to be applied to the clock inputs of the flip-flop A1 setting the flip-flop A1-1 so that its $\bar{Q}$ output is high and the Q output of flip-flop A1-2 is high. As a result, a "1" signal is applied via the NAND gate A4 to the reset inputs of the flip-flops A1 to reset the mode timer 618 to its initial or refractory state.

As explained above, the mode timer 618 provides an output signal indicative of which of the 3 states or modes, i.e., the refractory, sense or partial, or pulse width, in which the pacemaker 12" is operative. If a "1" signal appears at the output of the A5-1 NAND gate, there is an indication of pacemaker 12" is operative in its refractory mode, whereas if "1" signals appears at the output of the NAND gate A5-2 or A5-3, there is an indication that the pacemaker 12" is operative in its partial or pulse width mode, respectively. As would be well-known in the art, the output signal $T_W$ as derived from the A5-3 NAND gate may be applied to suitable triggerable pulse generating circuit means to trigger a stimulating pulse on terminal means which would be coupled to the patient's heart. In an illustrative example, the output signal $T_W$ could be applied to the input line 131a, as shown in FIG. 3A, whereby the transistor $Q_V$ is rendered conductive thus discharging the capacitor $C_V$ and applying a stimulating pulse to that portion of the patient's heart represented by the resistor R3. In a similar fashion, the output signal $T_R$ indicative of the refractory period could be applied to the input 132 to thereby couple the capacitor $C_V$ to the charging voltage $V_s$ during the refractory period. It is also contemplated that the signal $T_{PP}$ indicative of the sense or partial mode could also be applied to close the select switch 106a'. In this regard, it is noted that the select switch 106a' functions in a similar manner to the NAND gate A2-5, though there is not a precise correspondence between the elements of FIGS. 11a and b, and those of the circuitry FIG. 3a. It is readily apparent to one skilled in the art that the signals as derived from the mode timer 518 could be readily used to control the timing periods of an inhibited demand mode pacing. It is also contemplated that the circuitry of 11a and b could be expanded to time further periods to effect other modes of pacing including atrial and ventricular pacing.

Thus it is evident that the hardwire digital circuitry of the pacemaker 500, as shown in FIGS. 11A and B, operates in similar fashion to the microprocessor implemented pacemaker 12, as shown in FIG. 2, to enter into a single counter various counts indicative of the particular mode in which the pacemaker is operative, i.e., either refractory, sense, or pulse mode, and to make the value of the count dependent upon the level of battery depletion.

The digital circuitry of the present invention is characterized by the sequential use of a single counter for the timing functions of the pacemaker. It should be apparent that this feature can be emulated by a microprocessor and selected memory locations by decrementing a number stored in a selected memory location and testing when the number is decremented to zero.

Numerous changes may be made in the above-described apparatus and the different embodiments of the invention may be made without departing from the spirit thereof; therefore, it is intended that all matter contained in the foregoing description and in the accompanying drawings shall be interpreted as illustrative and not in a limiting sense.

What is claimed is:

1. A cardiac pacemaker for generating and applying stimulating pulses to a patient's heart comprising means for defining a plurality of available pacing modes, each comprised of a distinctive sequence and number of operating states of said pacemaker and means for defining control parameters defining characteristics of said operating states, said pacemaker further comprising:

electrode means, comprising means for coupling said stimulating pulses to said patient's heart and means for providing signals indicative of the condition of said patient's heart;

pulse generating circuit means for generating said stimulating pulses;

control means comprising:
  means for selecting one of said pacing modes;
  memory means for storing manifestations indicative of the sequences and numbers of operating states of said pacing modes and for storing said control parameters defining the characteristics of said operating states;
  means for sequentially operating said cardiac pacemaker in current operating states in accordance with said distinctive number and sequences of operating states of said selected one of said pacing modes;
  means responsive to said current operating states for addressing said memory means to readout and transfer addressed ones of said control parameters to said operating means; and
  mode control means responsive to said signals indicative of the condition of said patient's heart for selecting a predetermined one of said pacing modes, whereby said control means subsequently addresses the said memory means to read out and transfer addressed ones of said control parameters to said operating means defining characteristics of said operating states of said predetermined pacing mode.

2. A pacemaker according to claim 1 wherein said mode control means comprises means for detecting the occurrence of an arrhythmia based on said signals indicative of said heart's condition and wherein in response to detection of said arrhythmias, said mode control means operates to select said predetermined pacing mode.

3. A pacemaker according to claim 2 wherein said means for detecting an arrhythmia comprises means for measuring the relative timing between said signals indicative of the condition of said patient's heart and for detecting said arrhythmia if the delay between said signals is less than a predetermined period.

4. A pacemaker according to claim 1 above, wherein said plurality of electrode means comprises electrode means for coupling to a plurality of sites of said patient's heart, and wherein said pacing modes include a first pacing mode including a first operating state wherein a first one of said electrode means comprises means for applying stimulating pulses to said patient's heart and a second pacing mode including a second operating state in which a second one of said electrode means comprises means for applying stimulating pulses to the patient's heart.

5. A pacemaker according to claim 4, wherein said mode control means comprises means responsive to the failure of a said signal indicative of the condition of said patient's heart to occur within a current operating state of said first pacing mode for selecting said second pacing mode.

6. A cardiac stimulator for generating and applying electrical pulses to a patient's heart, comprising:
a first electrical pulse generator;
a first electrode coupled to said first pulse generator;
a second electrical pulse generator;
a second electrode coupled to said second pulse generator;
means for sensing signals indicative of the condition of said patient's heart;
means for defining a first stimulating mode comprising a distinctive first sequence and number of operating states of said stimulator, including a first operating state comprising delivery of an electrical pulse by said first pulse generator;
means for defining a second stimulating mode comprising a distinctive second sequence and number of operating states of said stimulator, including a second operating state comprising delivery of an electrical pulse by said second pulse generator;
means for defining control parameters defining characteristics of said operating states of said first and second stimulating modes;
memory means for storing manifestations indicative of said sequences and numbers of operating states of said first and second stimulating modes and for storing said control parameters defining characteristics of said operating states;
means for selecting said first or second stimulating mode;
means for sequentially operating said cardiac stimulator in current operating states in accordance with said distinctive number and sequences of operating states of said selected stimulating mode;
means responsive to said current operating states for addressing said memory means to readout and transfer said control parameters to said operating means; and
wherein said selecting means comprises means responsive to said signals indicative of the condition of said patient's heart for selecting said second stimulating mode.

7. A stimulator according to claim 6 wherein said selecting means comprises means for detecting the occurrence of an arrhythmia based on said signals indicative of the condition of said patient's heart and wherein in response to detection of said arrhythmia, said selecting means operates to select said second stimulating mode.

8. A stimulator according to claim 7 wherein said means for detecting an arrhythmia comprises means for measuring the relative timing between said signals indicative of the condition of said patient's heart and for detecting said arrhythmia if the delay between said signals is less than a predetermined period.

9. A stimulator according to claim 6, wherein said selecting means comprises means responsive to the failure of a said signal indicative of the condition of said patient's heart to occur within a current operating state of said first stimulating mode for selecting said second stimulating mode.

10. A cardiac stimulator for generating and applying electrical pulses to a patient's heart, comprising:
electrode means, comprising means for coupling said electrical pulses to said patient's heart and means for providing signals indicative of depolarizations of said patient's heart;
pulse generator means for generating said electrical pulses;
means for sensing signals indicative of the condition of said patient's heart;
means for defining a first stimulating mode comprising a distinctive first sequence and number of operating states of said stimulator;
means for defining a second stimulating mode comprising a distinctive second sequence and number of operating states of said stimulator;
means for defining control parameters defining characteristics of said operating states of said first and second stimulating modes;
memory means for storing manifestations indicative of said sequences and numbers of operating states of said first and second stimulating modes and for storing said control parameters defining characteristics of said operating states;
means for selecting said first or second stimulating mode;
means for sequentially operating said cardiac stimulator in current operating states in accordance with said distinctive number and sequences of operating states of said selected stimulating mode;
means responsive to said current operating states for addressing said memory means to readout and transfer said control parameters to said operating means; and
wherein said selecting means comprises means responsive to said signals indicative of depolarizations of said patient's heart for selecting said second stimulating mode.

11. A stimulator according to claim 10 wherein said selecting means comprises means for detecting the occurrence of an arrhythmia based on said signals indicative of the condition of said patient's heart and wherein in response to detection of said arrhythmia, said selecting means operates to select said second stimulating mode.

12. A stimulator according to claim 11 wherein said means for detecting an arrhythmia comprises means for measuring the relative timing between said signals indicative of the condition of said patient's heart and for detecting said arrhythmia if the delay between said signals is less than a predetermined period.

13. A stimulator according to claim 10, wherein said selecting means comprises means responsive to the failure of a said signal indicative of the condition of said patient's heart to occur within a current operating state of said first stimulating mode for selecting said second stimulating mode.

* * * * *